(12) United States Patent
Daksis et al.

(10) Patent No.: US 6,294,333 B1
(45) Date of Patent: Sep. 25, 2001

(54) FLUORESCENT INTENSITY ASSAY FOR PROTEIN OR PEPTIDE BINDING TO NUCLEIC ACIDS

(75) Inventors: Jasmine I. Daksis; Glen H. Erikson, both of Ontario (CA)

(73) Assignee: Ingeneus Corp., Bridgetown (BB)

( * ) Notice: Subject to any disclaimer, the term of this patent is extended or adjusted under 35 U.S.C. 154(b) by 0 days.

(21) Appl. No.: 09/224,505

(22) Filed: Dec. 31, 1998

(51) Int. Cl.[7] .............................. C12Q 1/68; C12P 19/34; C07H 21/00; C07H 21/04; C07H 21/02

(52) U.S. Cl. ............................ 435/6; 435/7.1; 435/91.1; 435/91.2; 536/22.1; 536/24.3; 536/24.31; 536/24.33; 536/25.32

(58) Field of Search ................................ 435/6, 7.1, 91.1, 435/91.2; 536/22.1, 24.3, 24.31, 24.32 24.83

(56) References Cited

U.S. PATENT DOCUMENTS

| | | |
|---|---|---|
| 4,743,535 * | 5/1988 | Carrico ..................................... 435/6 |
| 4,761,382 | 8/1988 | Woodhead et al. . |
| 5,187,106 | 2/1993 | Fritzsche et al. . |
| 5,445,935 | 8/1995 | Royer . |
| 5,747,247 * | 5/1998 | Kowalczykowski et al. . |
| 5,756,292 | 5/1998 | Royer . |
| 5,783,384 | 7/1998 | Verdine . |
| 5,846,729 | 12/1998 | Wu et al. . |

FOREIGN PATENT DOCUMENTS

| | | |
|---|---|---|
| 94/14980 | 7/1994 | (WO) . |
| 98/04923 | 2/1998 | (WO) . |
| 98/26093 | 6/1998 | (WO) . |

OTHER PUBLICATIONS

Kadonaga et al., "Isolation of cDNA Encoding Transcription Factor Sp1 and Functional Analysis of the DNA Binding Domain," Cell, 51:1079–1090, Dec. 24, 1987.

Bohmann et al., "Human Proto–Oncongen c–jun Encodes a DNA Binding Protein with Structural and Functional Properties of Transcription Factor AP–1," Science, 238:1386–1392, Dec. 1987.

Sturm et al., "The Ubiquitous octamer–binding protein Oct.–1 contains a POU domain with a homeo box subdomain," Genes & Development, 2:1582–1599, 1988.

Dalrymple et al., "DNA sequence of the herpes simplex virus type 1 gene whose product is responsible for transciptional activation of immediate early promoters," Nucleic Acids Research, vol. 13, No. 21, pp. 7865–7879, 1985.

Wilson et al., "The VP16 Accessory Protein HCF Is a Family of Polypeptides Processed from a Large Precursor Protein," Cell, 74:115–125, Jul. 16, 1993.

(List continued on next page.)

*Primary Examiner*—Kenneth R. Horlick
*Assistant Examiner*—Jeffrey Siew
(74) *Attorney, Agent, or Firm*—Caesar, Rivise, Bernstein, Cohen & Pokotilow, Ltd.

(57) ABSTRACT

A method for assaying binding between a fluorophore-labeled compound and an unlabeled compound is provided. The method includes detecting a quenching effect on fluorescence emitted by the fluorophore-labeled compound resulting from binding. The binding is specific and other than nucleobase to nucleobase. The method is conducted without separating complexes of the fluorophore-labeled compound and the unlabeled compound from the fluorophore-labeled compound prior to quenching effect detecting, and without providing a signal quenching agent to quench fluorescent light. Preferably, the fluorophore-labeled compound is a nucleic acid and the unlabeled compound is a protein. The method can be used for a variety of applications, including screening for drug candidates having optimum binding properties, and quantifying the binding affinity of DNA binding proteins for nucleic acids.

27 Claims, 9 Drawing Sheets

OTHER PUBLICATIONS

Brown et al., "Fluorescence spectroscopy as a tool to investigate protein interactions," Current Opinion in Biotechnology, 1997, 8:45–49.

Hill et al., "Fluorescence Approaches to Study of Protein–Nucleic Acid Complexation," Methods in Enzymology, 278:390–416, 1997.

* cited by examiner

FLUORESCENT INTENSITY ASSAY FOR PROTEIN OR PEPTIDE BINDING TO NUCLEIC ACIDS

FIELD OF THE INVENTION

This invention relates to biopolymer binding assays, and more particularly to methods for assaying binding between nucleic acids and peptides or proteins using fluorescent intensity data.

BACKGROUND OF THE INVENTION

Protein-nucleic acid complexes are known to play an important role in a variety of biological processes. See, e.g., Hill et al. "Fluorescence Approaches to Study of Protein-Nucleic Acid Complexation," 278 Methods in Enzymology 390 (1997). For example, DNA-binding proteins are known to play an important role in gene regulation. Genes are typically regulated at the transcriptional level by DNA-binding proteins, which are referred to as transcription factors. Transcription factors regulate gene expression by specifically binding to a target nucleic acid sequence in promoter DNA.

Due to the biological importance of protein-nucleic acid interaction, a variety of methods for studying protein-nucleic acid binding characteristics have been proposed. See, e.g., Hill et al. and the references cited therein.

U.S. Pat. No. 5,783,384 to Verdine discloses methods for determining the affinity of a DNA-binding protein for a target nucleic acid sequence. Verdine teaches methods comprising providing a reversible bond between a DNA-binding protein and a target nucleic acid sequence, and determining the relative strength of the reversible bond (and thus the affinity of the protein for the nucleic acid) by breaking it under supervised conditions. The more stringent the conditions necessary to break the bond, the higher the affinity of the protein for the nucleic acid. Verdine does not disclose or suggest fluorescence-based binding assays.

U.S. Pat. No. 5,445,935 to Royer discloses fluorescence-based methods for studying protein-oligonucleotide binding; however, the teachings of the patent are solely limited to fluorescent anisotropy techniques. Basically, anisotropy measures rotational diffusion events of free DNA or protein-bound DNA, as well as the local motions of a fluorophore attached to the DNA via a linker arm. Free DNA rotates quickly, depolarizes the light more readily and exhibits a low anisotropy value. In contrast, protein-bound DNA rotates slowly relative to the lifetime of the fluorophore, depolarizing the light only slightly and thus exhibiting a relatively high anisotropy value.

However, there are significant drawbacks to anisotropy-based assays. The degree of change in anisotropy as a function of binding is not as predictable as the proponents of anisotropy-based methods assert. Interpretation of anisotropy data to conform inconsistent data to theoretical expectations can require more effort than is desirable in an analytical method, particularly when the method is to be automated.

Radioactive labeling remains the most popular method for analyzing protein-nucleic acid interaction, despite being relatively slow, a health and environmental hazard, and relatively labor-intensive. Conventional radioactive labeling methods typically require radioactively end-labeling DNA probes with $^{32}P$ using specialized enzymes. Purification of labeled DNA from unincorporated $^{32}P$ involves polyacrylamide gel electrophoresis, overnight elution, gel filtration and concentration steps. Since the half-life of $^{32}P$ is only 14 days, radio-labeling is required approximately every three weeks for each probe. Moreover, protein-$^{32}P$-DNA complexes need to be separated from unbound $^{32}P$-DNA by native polyacrylamide gel electrophoresis. Gels are then dried and analyzed by autoradiography or phosphoimaging.

Thus, a need has existed in the art for a simple, effective and rapid method for analyzing peptide-nucleic acid and protein-nucleic acid interaction.

All references cited herein, including U.S. Pat. No. 5,846,729 and U.S. patent applications Ser. Nos. 08/807,901 and 08/870,370 (respectively filed Feb. 27, 1997 and Jun. 6, 1997), are incorporated herein by reference in their entireties.

SUMMARY OF THE INVENTION

The invention provides a method for assaying binding between at least one fluorophore-labeled compound and at least one unlabeled compound. The method comprises detecting a quenching effect on fluorescence emitted by said at least one fluorophore-labeled compound resulting from said binding, wherein said binding is specific and other than nucleobase to nucleobase. The method is preferably conducted without separating complexes of said at least one fluorophore-labeled compound and said at least one unlabeled compound from said at least one fluorophore-labeled compound prior to said quenching effect detecting, aid without providing a signal quenching agent to quench said emitted fluorescence.

BRIEF DESCRIPTION OF THE DRAWINGS

The invention will be described in conjunction with the following drawings in which like reference numerals designate like elements and wherein.

DETAILED DESCRIPTION OF PREFERRED EMBODIMENTS

Figure 1A:
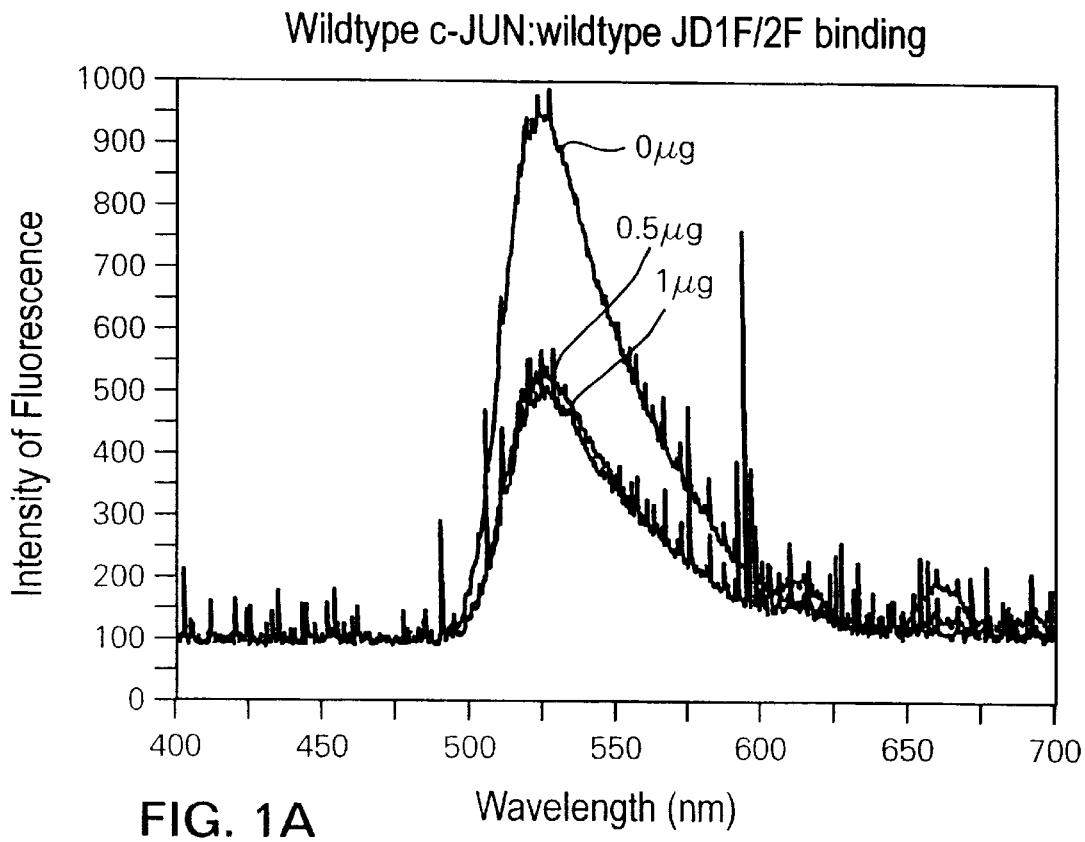
FIGS. 1A, 1B, 1C, 1D, 2A, 2B, 3A, 3B, 4A, 4B, 5A, 5B, 6A, 6B, 7A, 7B, 8A, and 8B are fluorescent spectra.

The invention provides a method for assaying specific binding between at least one protein sequence and at least one nucleic acid sequence, wherein said at least one protein sequence and/or said at least one nucleic acid sequence contains at least one fluorophore. The method comprises detecting a fluorescent intensity quenching effect on the at least one fluorophore resulting from the specific binding to form at least one protein-nucleic acid complex. Preferably, the fluorophore is attached to the at least one nucleic acid sequence prior to binding to the at least one protein sequence.

Unlike fluorescent anisotropy levels, which increase when a protein binds to a DNA or RNA oligonucleotide, the fluorescent emission intensity decreases upon complex formation.

A preferred method for detecting quenching (and thus assaying binding) comprises: (a) providing a test medium comprising the at least one nucleic acid sequence and the at least one protein sequence; (b) irradiating the test medium with radiation effective to cause the at least one fluorophore to emit fluorescent light; and (c) comparing a fluorescent intensity of the fluorescent light with a reference fluorescent intensity of a reference medium substantially identical to the test medium except that the reference medium is devoid of the at least one protein sequence, wherein the quenching effect and the specific binding are detected when the fluorescent intensity is less than the reference fluorescent intensity. Quenching is indicative of the formation of a protein-nucleic acid complex through specific binding.

As defined herein, specific binding between at least one protein sequence and at least one nucleic acid sequence excludes complementary (i.e., Watson-Crick) base pairing between peptide nucleic acids and nucleic acids, but includes all other types of specific binding between proteins (for purposes of this invention, the term "protein" is defined in its broadest sense as including, e.g., peptides (e.g., peptides, dipeptides, tripeptides, etc.), polypeptides, proteins and multi-protein complexes) and nucleic acids (e.g., dsDNA, ssDNA, RNA, ssRNA, dsRNA, mRNA, hnRNA, tRNA, rRNA, ssDNA:RNA hybrids, dsDNA:RNA hybrids, nucleic acid analogues and oligonucleotides).

A variety of protein-nucleic acid complexes can be assayed with the method of the invention. The invention can be used to analyze binding characteristics (including the presence or absence of binding, and the binding affinity) between a nucleic acid and, e.g., a peptide, a protein, or a multi-protein complex. Suitable proteins for analysis include, e.g., wild-type, mutant, isolated, in vitro translated, and/or synthesized. The invention is particularly suitable for analyzing binding of DNA-binding protein to dsDNA. Test samples need not be 100% pure, but rather, can comprise, e.g., a purified preparation, a synthesized preparation, a semi-purified protein extract, a crude protein extract, or an in vitro translated preparation.

Embodiments of the invention analyze the binding characteristics of multiple protein complexes having the same or different proteins bound to single or multiple binding sites on the nucleic acid sequence. Multi-protein:DNA complexes are more prevalent in nature and more biologically significant than single protein:DNA complexes or homodimer:DNA complexes. Using the invention, it is possible to detect whether the two (or more) interacting proteins bind to their respective DNA sites independently, cooperatively or synergistically. For example, the invention can measure the binding of two proteins to two DNA sites separated by intervening DNA sequences, that loop out when the two bound proteins interact with one another.

The components of the binding complexes need not be wild-type only or perfect matches. For example, the invention can assay binding between a mutant protein and a mutant DNA binding sequence or between a mutant protein with altered binding affinity to a wild-type DNA binding site.

The invention enables detecting the binding of a first unlabeled compound to a second unlabeled compound by detecting a change in the binding characteristics (as indicated by a change in the fluorescent intensity) between the first unlabeled compound and a labeled compound. For purposes of this invention, such detection is referred to as "secondary binding" detection, or in its broader sense, "indirect binding" detection. In theory, the invention enables tertiary binding detection, quaternary binding detection, and so forth, provided that each additional level of binding Produces a significant change in binding between the labeled compound and the first unlabeled compound.

Similarly, the invention also enables detecting the binding of an unlabeled compound to at least one member of a complex of complexed compounds, wherein at least one of the complexed compounds is labeled for fluorescent intensity measurements. The labeled compound and the unlabeled compound need not even directly interact for detection to occur. The essential point is that the invention enables detecting a condition through its indirect or direct influence on the binding characteristics of a labeled probe to a target.

Thus, the invention enables detecting the binding of an antibody (i.e., the "second unlabeled compound") to a specific protein (i.e., the "first unlabeled compound") against which the antibody is directed, wherein the specific protein is either directly bound to the labeled DNA sequence, or is present in a multi-protein:DNA complex and thus interacting with one or more other proteins in the complex, but not necessarily directly interacting with the labeled DNA. Addition of specific antibodies to protein:DNA complexes (especially multi-protein:DNA complexes) is a widely used technique to identify the presence of unknown proteins in protein:DNA complexes. The binding of the antibody will either prevent the protein:DNA complex from forming (resulting in no change in intensity when compared to free DNA) or will result in an antibody: protein: DNA complex that should decrease the intensity of fluorescence even more than the protein:DNA complex.

The invention further enables detecting direct and indirect binding of a labeled nucleic acid to other sequence-specific binding molecules, such as peptides, peptidomimetics, complex carbohydrates or other oligomers.

The invention is useful for a vast number of purposes, including designing and/or selecting molecules that bind in a site-specific manner to desired DNA or other types of sequences, or that alter binding of other molecules. The invention thus provides a method for identifying and evaluating new substances, or drugs, that have a specific binding activity, or that predictably alter the binding characteristics of other binding pairs/complexes. For example, a substance with DNA binding specificity can be identified which binds to promoter DNA, thus acting as a transcriptional blocker. This newly-identified transcription blocking substance can be used in both in vitro and in vivo transcriptional processes.

The method of the invention can be conducted without separating the at least one Protein-nucleic acid complex from the at least one protein sequence and the at least one nucleic acid sequence prior to the fluorescent intensity detecting, and without providing a signal quenching agent on the at least one protein or on the at least one nucleic acid sequence.

The method does not require the use of radioactive probes, which are hazardous, tedious and time-consuming to use, and need to be constantly regenerated. Probes of the invention are preferably safe to use and stable for years. Accordingly, probes can be made or ordered in large quantities and stored.

The method of the invention does not require a gel separation step, thereby allowing double the amount of samples to be tested and analyzed in just half a day. Quantitative analyses are simple and accurate.

The invention will be illustrated in more detail with reference to the following Examples, but it should be understood that the present invention is not deemed to be limited thereto.

EXAMPLES

The Examples demonstrate the binding of three different classes of DNA-binding proteins to their respective DNA recognition sites, as evidence that the laser-based assay of the invention is applicable to all classes of DNA-binding proteins. The three representative proteins selected for the Examples are c-JUN (Examples 1–3 and 5), Sp 1 (Example 4) and Oct-1 (Examples 6–7).

Example 1 c-JUN is a member of the AP-1 family of transcription factors that bind and regulate AP-1 DNA-binding sites naturally present in promoter or enhancer sequences of many cellular and viral genes. See, e.g., Bohmann et al., "Human proto-oncogene c-jun encodes a DNA binding protein with structural and functional properties of transcription factor AP-1." 238 Science 1386–1392 (1987). Furthermore, the human c-JUN protein belongs to a class of proteins (that include c-FOS and c-MYC), designated proto-oncoproteins, which when deregulated and activated, cause tumorigenesis and cancer c-JUN, c-FOS and c-MYC constitute a specific group of DNA-binding proteins, whose DNA-binding domain consists of a region rich in basic amino acids (commonly called the "basic region" or "basic domain") that lies immediately adjacent to a structural domain, designated the "leucine zipper". The leucine zipper consists of 4 to 5 leucine residues (c-JUN has 5), that are separated at regular intervals of 7 amino acids, which form bimolecular coiled-coiled structures. Specific contact with its palindromic DNA sequence occurs primarily via the basic region. The leucine zipper allows dimerization of c-JUN to itself, forming c-JUN:c-JUN homodimers, or to c-FOS forming c-JUN:c-FOS heterodimers. Homodimers of c-JUN bend DNA 79° toward the minor groove of a DNA helix, while c-JUN:c-FOS heterodimers bend DNA 94° in the opposite orientation, towards the major groove. A fully functional DNA-binding domain requires both the basic region and the leucine zipper. As pure human c-JUN protein is used in the following assays, the examples show binding of c-JUN:c-JUN homodimers to a single AP-1 site (JD1F/2F).

A fluorescein labeled wild-type dsDNA oligonucleotide, JD1F/2F, containing a consensus 7 bp AP-1 DNA binding site, was derived from the promoter sequence of the human collagenase gene. Complementary 5'-fluorescein labeled ssDNA 17-mers JD1F and JD2F, having 5 nucleotides flanking both ends of the consensus AP-1 site, were synthesized on a PerSeptive Biosystems Expedite nucleic acid synthesizer and purified by HPLC. Equimolar amounts of JD1F and JD2F oligos were annealed in 10 mM Tris, pH 7.5, 100 mM NaCl, 1 mM EDTA by denaturation at 95° C. for minutes, followed by incubation at 42° C., 35° C. and 21° C. for 40 minutes each. Annealed oligos were ethanol precipitated for 2 hours at −20° C., pelleted by centrifugation at 14K rpm for 20minutes at 0° C., washed with 100% ethanol, repelleted at 14K rpm for 20 minutes at 0° C., dried and dissolved in ddH$_2$O at a final concentration of 100 ng/μl. The dsDNA oligos formed had a single fluorescein molecule on both 5' ends.

Sequence for wild-type JD1F (SEQ ID NO: 1):
5'-Flu-GTG TCT GAC TCA TGC TT-3'
Sequence for wild-type JD2F (SEQ ID NO:2):
5'-Flu-AAG CAT GAG TCA GAC AC-3'

Mutant dsDNA 17-mer JD3F/4F was identical in sequence to wild-type JD1F/2F, except for a single base pair change (underlined) from GC to TA within the wild-type AP-1 consensus DNA-binding site.

Sequence for mutant JD3F (SEQ ID NO:3):
5'-Flu-GTG TCT TAC TCA TGC TT-3'
Sequence for mutant JD4F (SEQ ID NO:4):
5'-Flu-AAG CAT GAG TAA GAC AC-3'

The c-JUN :DNA binding reaction mixture (30 μl) contained the following: 9.25 mM HEPES, pH 7.9, 2.23 mM MgCl$_2$, 0.03 mM EDTA, 50 mM NaCl, 5.0 mM DTT, 3.75% (v/v) glycerol, 0.15 μg/μl bovine serum albumin (BSA), 0–2.0 μg pure c-JUN protein (Promega, Madison, Wis.) or 0–400 ng pure c-JUN peptide, and 0.075 pmole 5'-fluorescein labeled dsDNA oligonucleotide. When full-length c-JUN was used, 3 ng/μl poly(dI)-poly(dC) was included in the reaction mix, and added before the addition of protein and fluorescein-labeled DNA. The examples in FIGS. 1B and 1D contained 50 mM KCl in lieu of 50 mM NaCl. Wild-type and mutant c-JUN DNA-binding domain peptides were generously supplied by Dr. Dirk Bohmann (European Molecular Biology Laboratory, Heidelberg, Germany). The reaction mixtures were incubated at 21° C. for 30 minutes, placed into a quartz cuvette, irradiated with an argon ion laser beam having a wavelength of 488 nm and monitored for fluorescent emission.

The wild-type c-JUN DNA-binding domain peptide consisted of the C-terminal 132 amino acid residues of c-JUN (from Gln 209 to Phe 340). The c-JUN mutant 14 DNA-binding domain peptide was identical in sequence to the wild-type peptide, except for a two amino acid substitution (underlined) that converted lysine to isoleucine at position 277 and cysteine to aspartic acid at position 278, within the central basic domain.

Sequence for wild-type c-JUN peptide (SEQ ID NO:5):

```
    210         220         230         240
QPQQQQQPPHHLPQQMPVQHPRLQALKEEPQTVPEMPGE 250         260         270         280
TPPLSPIDMESQERIKAERKRMRNRIAASKCRKRKLERIA 290         300         310         320
RLEEKVKTLKAQNSELASTANMLREQVAQLKQKVMNHV 330         340
NSGCQLMLTQQLQTF
```

Sequence for mutant 14 c-JUN peptide (SEQ ID NO:6):

```
    210         220         230         240
QPQQQQQPPHHLPQQMPVQHPRLQALKEEPQTVPEMPGE 250         260         270         280
TPPLSPIDMESQBRIKABRKRMRNRIAASIDRKRKLBRIA 290         300         310         320
RLBBKVKTLKAQNSELASTANMLRBQVAQLKQKVMNHV 330         340
NSGCQLMLTQQLQTF
```

Figure 1B:
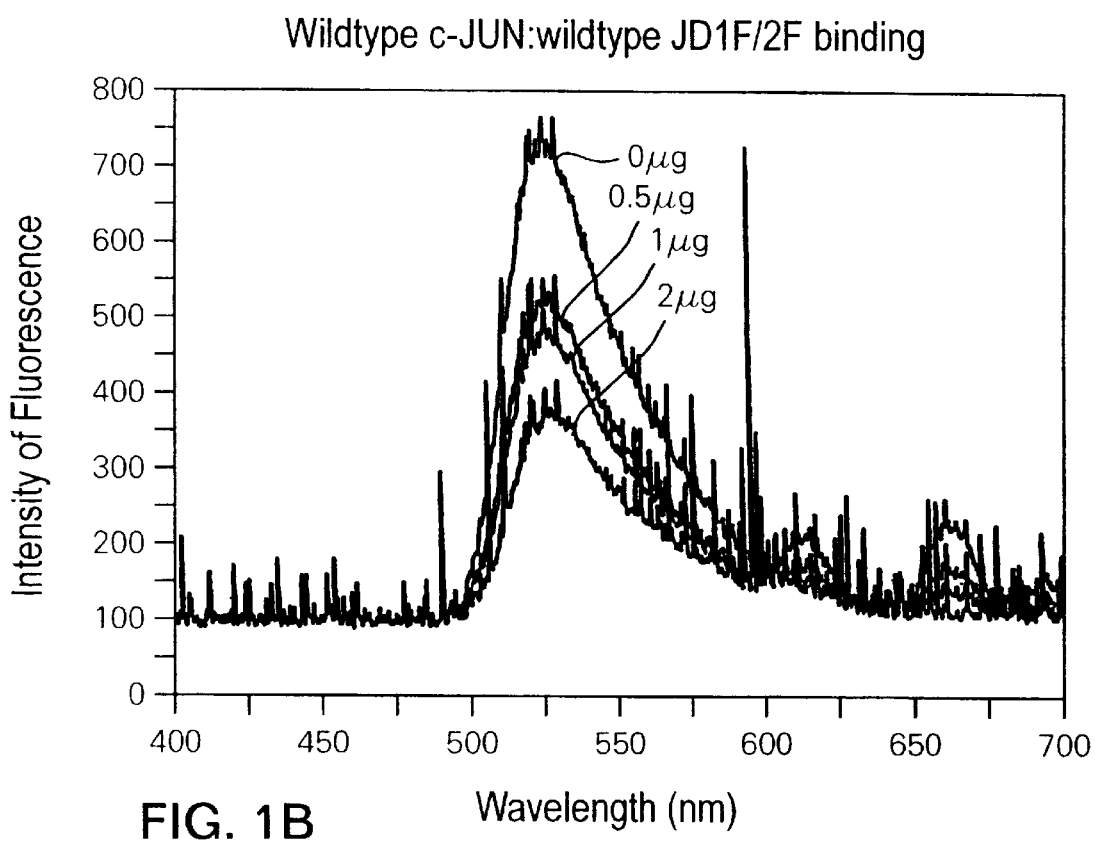
Figure 1C:
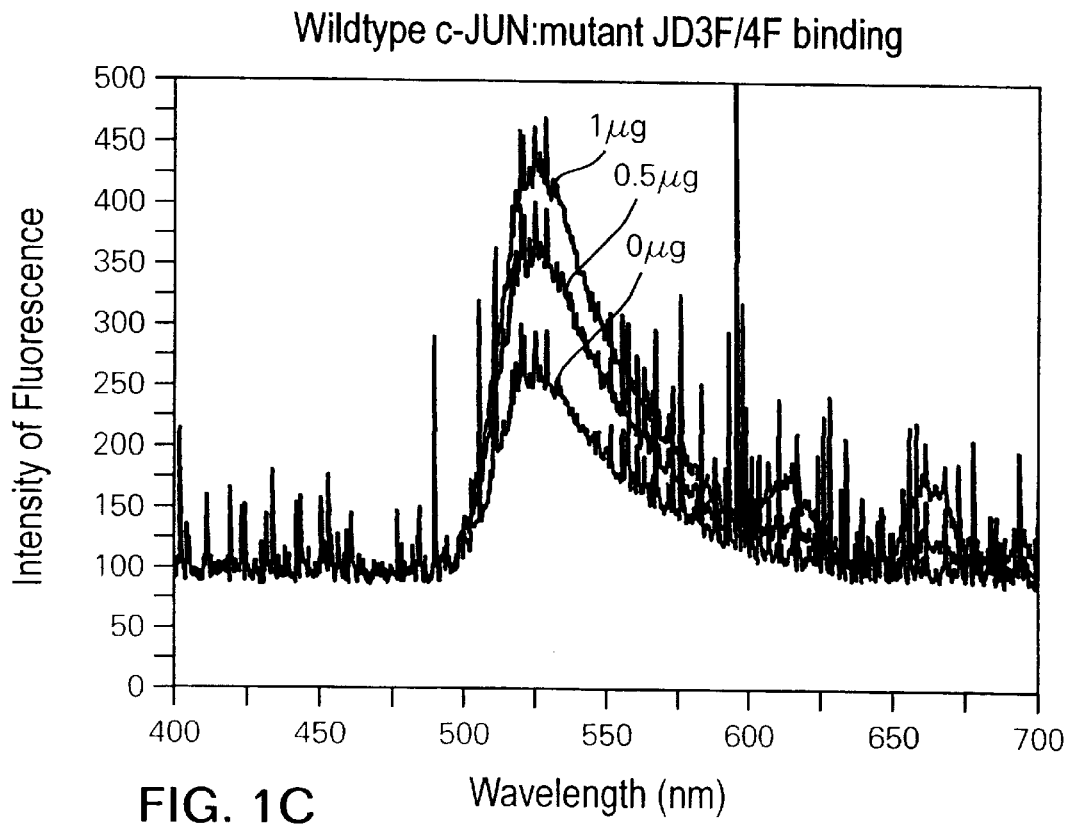
Figure 1D:
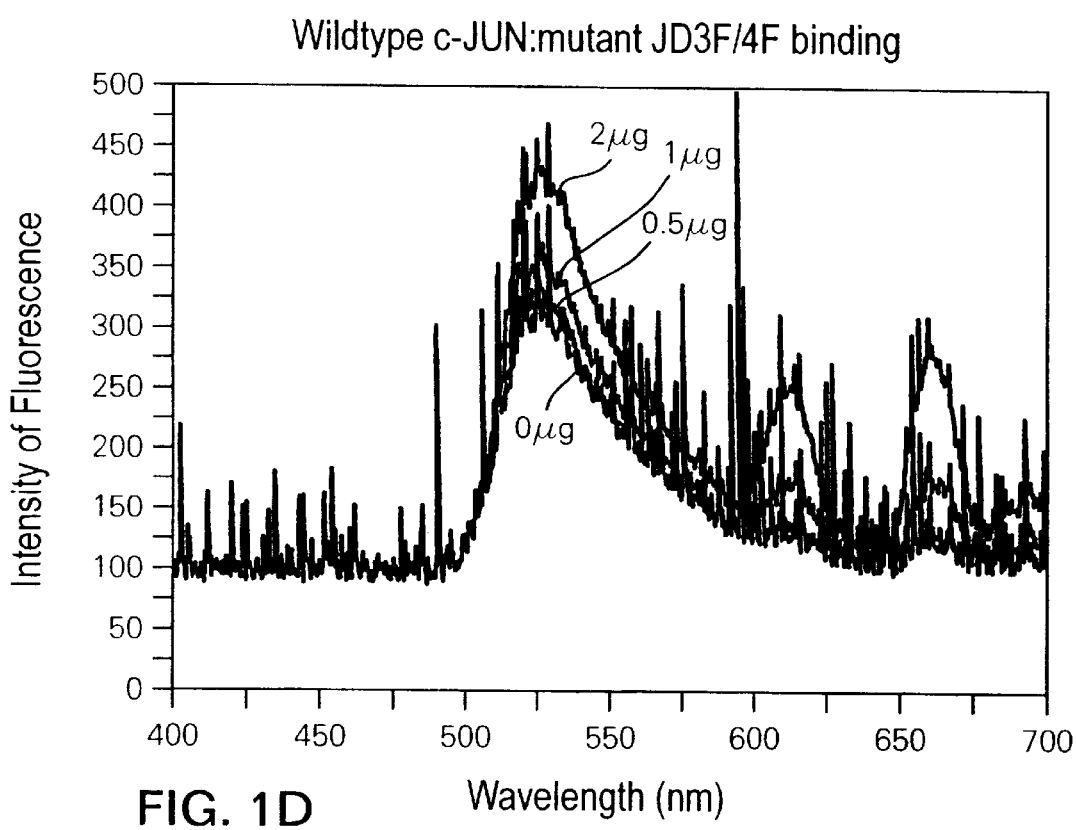

The fluorescence spectra obtained for the binding of 2 μg, 1 μg or 0.05 μg full length c-JUN to 0.075 pmole wild-type JD1F/2F or 0.075 pmole mutant JD3F/4F are shown in FIGS. 1A–1D. The DNA concentration was kept constant at 2.5 fmole/μl for every sample tested. All samples, whether DNA alone, or in the presence of c-JUN, were tested under identical reaction conditions. The maximum fluorescent intensity occurred at 525 nm, since the fluorophore used was fluorescein. The maximum intensity observed when 1 μg or 0.05 μg c-JUN was bound to JD1F/2F was 54% and 49% lower, respectively, than that observed with JD1F/2F alone (FIG. 1A). A 55% decrease in intensity resulted when 2 μg c-JUN was bound to wild-type JD1F/2F (data not shown) The similar decreases in intensity obtained with both 1 μg and 2 μg c-JUN, suggest that saturation levels of binding were achieved by addition of 1 μg protein.

To test c-JUN's preference for binding DNA under different salt conditions, the above experiment was performed simultaneously in a reaction buffer containing 50 mM KCl instead of 50 mM NaCl (FIG. 1B). When 2 μg c-JUN was bound to wild-type JD1F/2F in the KCl reaction buffer, a 57% decrease in intensity was observed, compared to the level achieved with DNA alone. 1 µg and 0.5 µg c-JUN bound to wild-type JD1F/2F in the 50 mM KCl buffer, yielded a 40% and 34% decrease, respectively, suggesting below saturation levels of binding. Therefore, c-JUN binds to its AP-1 site with higher binding affinity in a 50 mM NaCl reaction mix than in a 50 mM KCl reaction mix. Thus, the laser binding assay according to the invention could not only reliably detect c-JUN:DNA binding, but could also identify preferential binding conditions.

During the same experiment, when the exact same amounts of c-JUN were reacted with 0.075 pmole mutant JD3F/4F in the 50 mM NaCl reaction mix (FIG. 1C) or the 50 mM KCl reaction mix (FIG. 1D), no decrease in fluorescent intensity was observed in every sample, indicating non-binding of protein to the mutated DNA sequence. These mutant DNA binding studies confirm the specificity of both the c-JUN:wild-type DNA binding conditions and the laser detection method.

Identical results were obtained when the emitted fluorescent intensities were measured at three different integration times (data not shown), demonstrating consistent results irrespective of the integration time.

Example 2

Full length c-JUN protein is 40 KDa or 340 amino acids in size. The DNA-binding domain of c-JUN is localized to the C-terminal 132 amino acid residues of c-JUN (from glutamine at residue 209 to phenylalanine at residue 340), and is able to bind DNA with similar binding affinity as the full length protein.

Figure 2A:
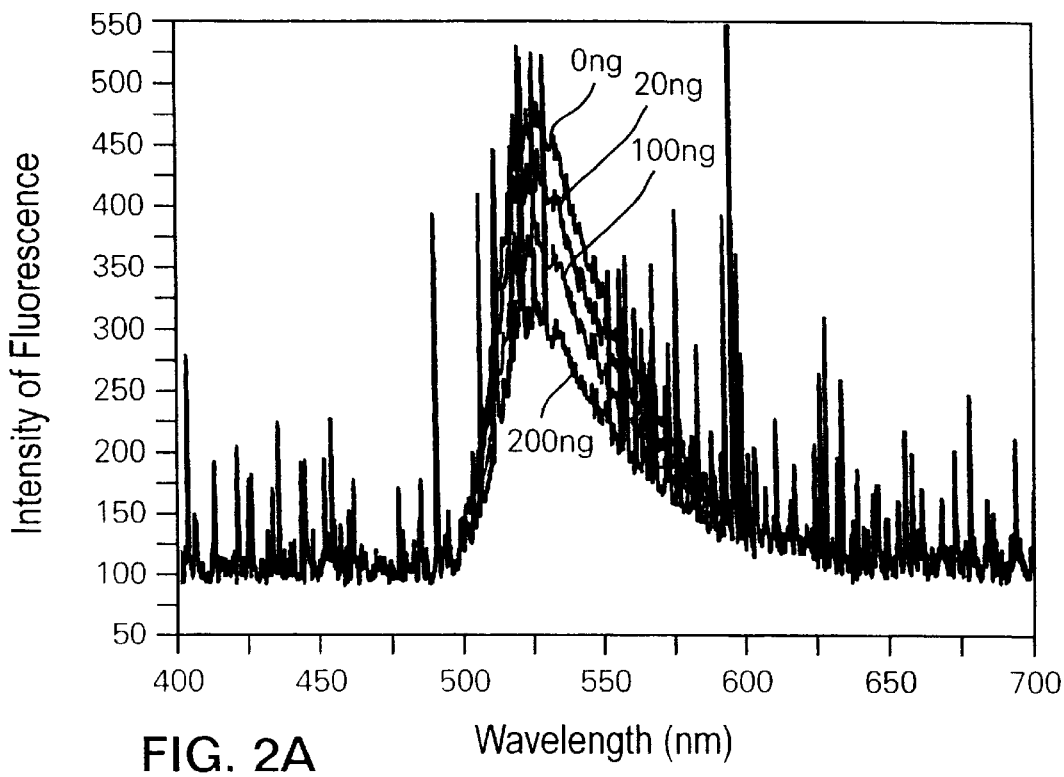
Figure 2B:
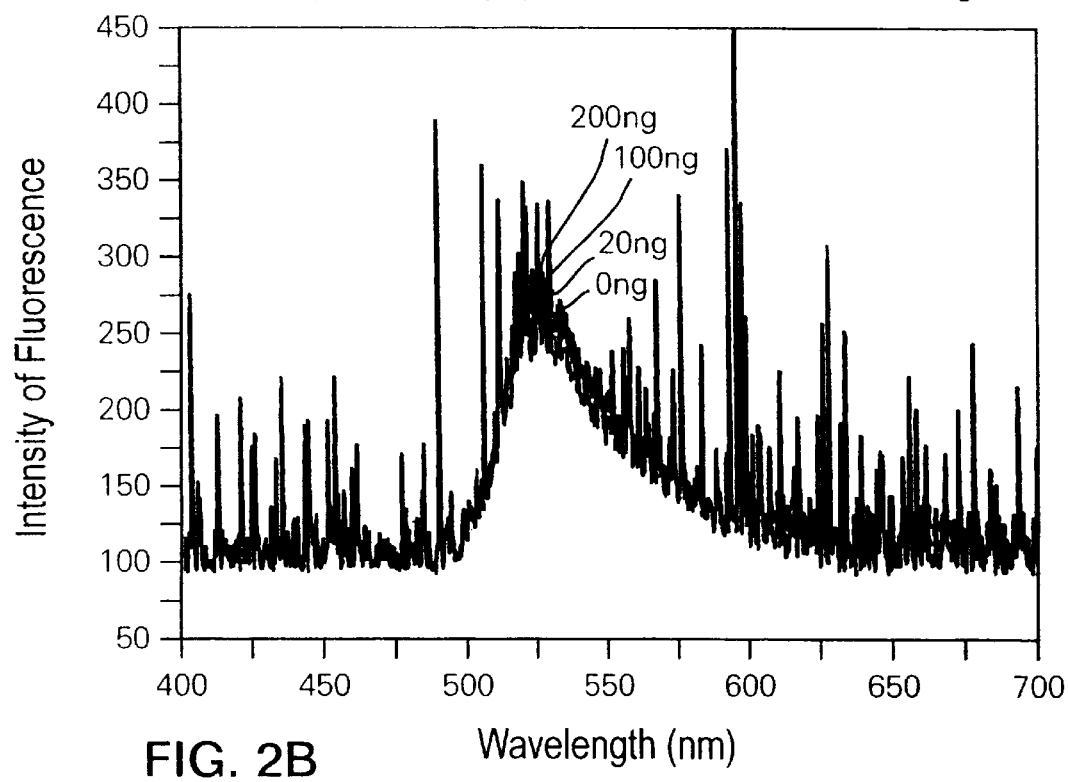

FIGS. 2A–2B demonstrate that the laser assay can also detect specific binding by a pure protein peptide consisting of only this 132 amino acid DNA-binding domain. 20 ng, 100 ng and 200 ng of wild-type c-JUN DNA-binding domain peptide bound to 0.075 pmole wild-type JD1F/2F in the 50 mM NaCl reaction mix, resulted in a 13%, 28% and 43% decrease in fluorescent intensity, respectively, compared to the intensity emitted by JD1F/2F alone (FIG. 2A). The fact that the binding of just 20 ng of c-JUN peptide to 0.075 pmole DNA could be reliably detected, demonstrates the high sensitivity of the laser assay. Moreover, the peptide:DNA binding assay is quantitative since increasing amounts of c-JUN peptide resulted in progressively more binding to wild-type DNA.

By contrast, 20 ng, 100 ng and 200 ng wild-type c-JUN peptide did not bind mutant JD3F/4F, resulting in minor increases in fluorescent intensity above that observed with mutant DNA alone (FIG. 2B), confirming the specificity of the laser binding assay.

The 43% decrease in fluorescent intensity observed for 200 ng of c-JUN peptide bound to JD1F/2F, is less than the 54% and 49% decreases observed for 1 µg and 0.5 µg full length c-JUN protein, respectively, as predicted. One would expect to get less static quenching occurring with a peptide, than with a full length protein, since less mass of protein would absorb the emitted fluorescent light in a peptide.

Example 3

Figure 3A:
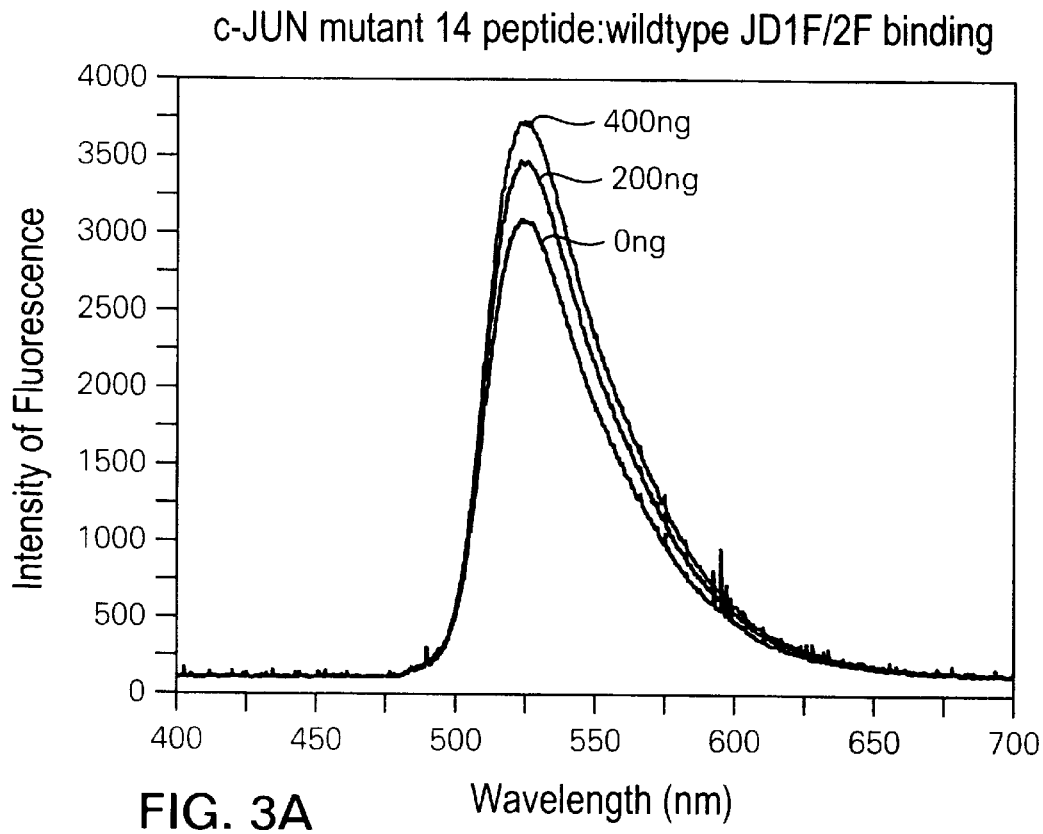
Figure 3B:
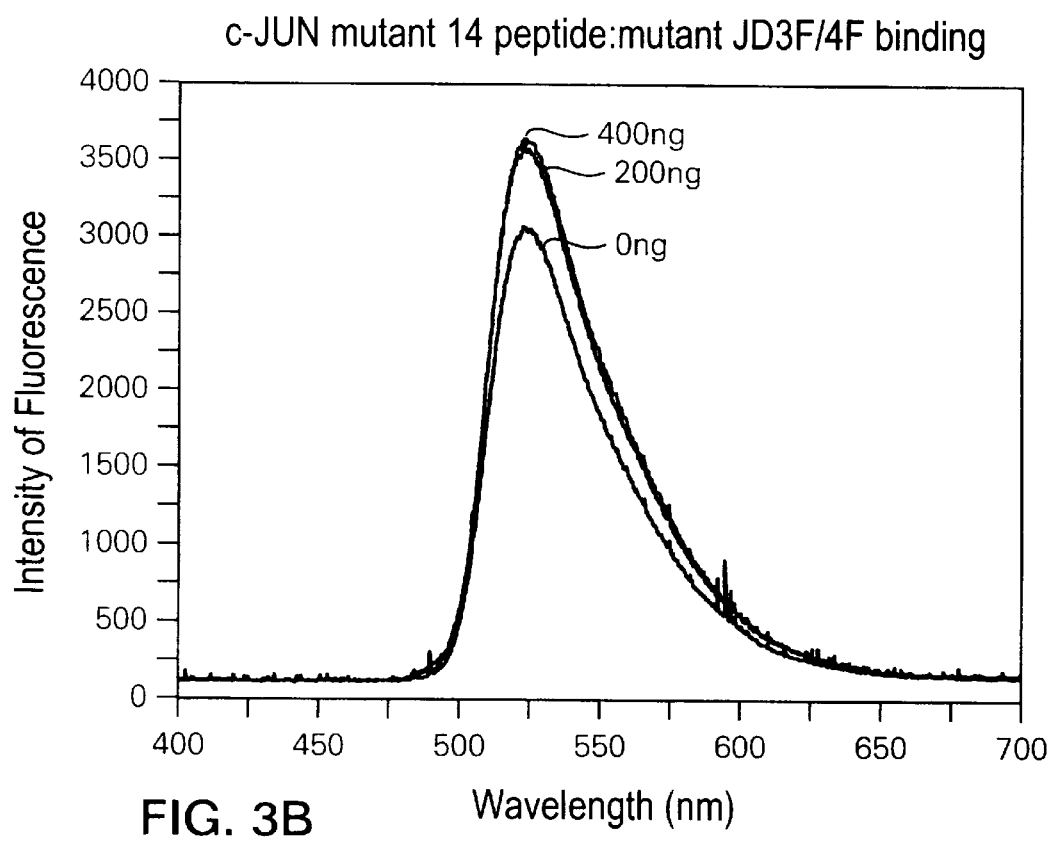

The specificity of the laser binding assay was further tested by reacting a mutant c-JUN DNA-binding domain peptide with wild-type or mutant DNA. Specific mutations in the basic domain of c-JUN abolish DNA binding without affecting dimerization, whereas specific mutations in the leucine zipper prevent both dimerization and DNA binding. The fluorescence spectra obtained when 200 ng and 400 ng of pure c-JUN mutant 14 peptide, possessing a two amino acid substitution within the basic domain of c-JUN, was reacted with 0.075 pmole wild-type JD1F/2F or mutant JD3F/4F, are illustrated in FIG. 3A and FIG. 3B, respectively. No decrease in fluorescent intensity was observed for JD1F/2F or JD3F/4F, even when a vast excess of c-JUN mutant 14 Peptide was present, clearly demonstrating disruption of DNA binding, and further proving the specificity of the laser binding assay.

Example 4

Sp1 belongs to a significant class of DNA-binding proteins designated zinc finger DNA-binding proteins. See, e.g., Kadonaga et al., "Isolation of cDNA encoding transcription factor Sp1 and functional analysis of the DNA binding domain." 51 Cell 1079–1090 (1987). Sp1 controls the transcription of a large number of viral and cellular promoters or enhancers, including the HIV-I long terminal repeat (LTR). The number, spacing, orientation and sequence of Sp1 binding sites vary widely between promoters, resulting in high, medium or low affinity binding sites. Although Sp1 is a relatively large protein (95 KDa and 105 KDa in its glycosylated and phosphorylated form), its DNA-binding activity is localized near the C-terminus of the protein (from cysteine at residue 539 to histidine at residue 619). This region contains three contiguous Zn(II) finger motifs, which are metalloprotein structures that interact with DNA. Sequence specificity of DNA binding is conferred entirely by the three Zn(II) fingers. Finger 3 is the most critical finger (with respect to binding affinity), followed by finger 2 and lastly finger 1. Two cysteine and two histidine residues bind a Zn(II) ion to form each finger. Removal of zinc collapses the secondary structure of the three zinc fingers. The fingers in this class of DNA-binding proteins have a consensus sequence of Cys-$X_{2,4}$-Cys-$X_3$-Phe-$X_5$-Leu-$X_2$-His-$X_3$-His, referred to as $Cys_2/His_2$ fingers. A second type of Zn(II) finger motif, referred to as $Cys_2/Cys_2$ fingers with the form of Cys-$X_2$-Cys-$X_{13}$-Cys-$X_2$-Cys, are found in other DNA-binding proteins, such as many hormone receptors.

A wild-type fluorescein labeled dsDNA oligonucleotide, JD11F/12F, containing a single consensus 10 bp Sp1 DNA binding site, was derived from the promoter sequence of the human metallothionein-$II_A$ gene. Complementary 5'-fluorescein labeled ssDNA 20-mers JD11F and JD 12F were synthesized, purified and annealed as above.

Sequence for wild-type JD11F (SEQ ID NO:7):
5'-Flu-CCG GCC GGG GCG GGG CTT TT-3'
Sequence for wild-type JD12F (SEQ ID NO:8):
5'-Flu-AAA AGC CCC GCC CCG GCC GG-3'

Mutant dsDNA 20-mer JD13F/14F was identical in sequence to wild-type JD11F/12F, except for a 6 bp change (underlined) which converted the consensus Sp1 binding site GGG GCG GGG C to TAA ATA GGG C.

Sequence for mutant JD13F (SEQ ID NO:9):
5'-Flu-CCG GCC <u>TAA ATA</u> GGG CTT TT-3'
Sequence for mutant JD14F (SEQ ID NO:10):
5'-Flu-AAA AGC CC<u>T ATT TA</u>G GCC GG-3'

The Sp1:DNA binding reaction mixture (30 µl) contained the following: 25 mM HEPES, pH 7.8, 100mM KCl, 100 µM $ZnSO_4$, 1 mM DTT, 20% (v/v) glycerol, 0.05 µg/µl BSA, 0–200 ng pure Sp1 protein (Promega) and 0.1 pmole 5'-fluorescein labeled dsDNA oligonucleotide. The reaction mixes were incubated at 0° C. for minutes, placed into a quartz cuvette, irradiated with an argon ion laser beam having a wavelength of 488 nm and monitored for fluorescent emission.

Figure 4A:
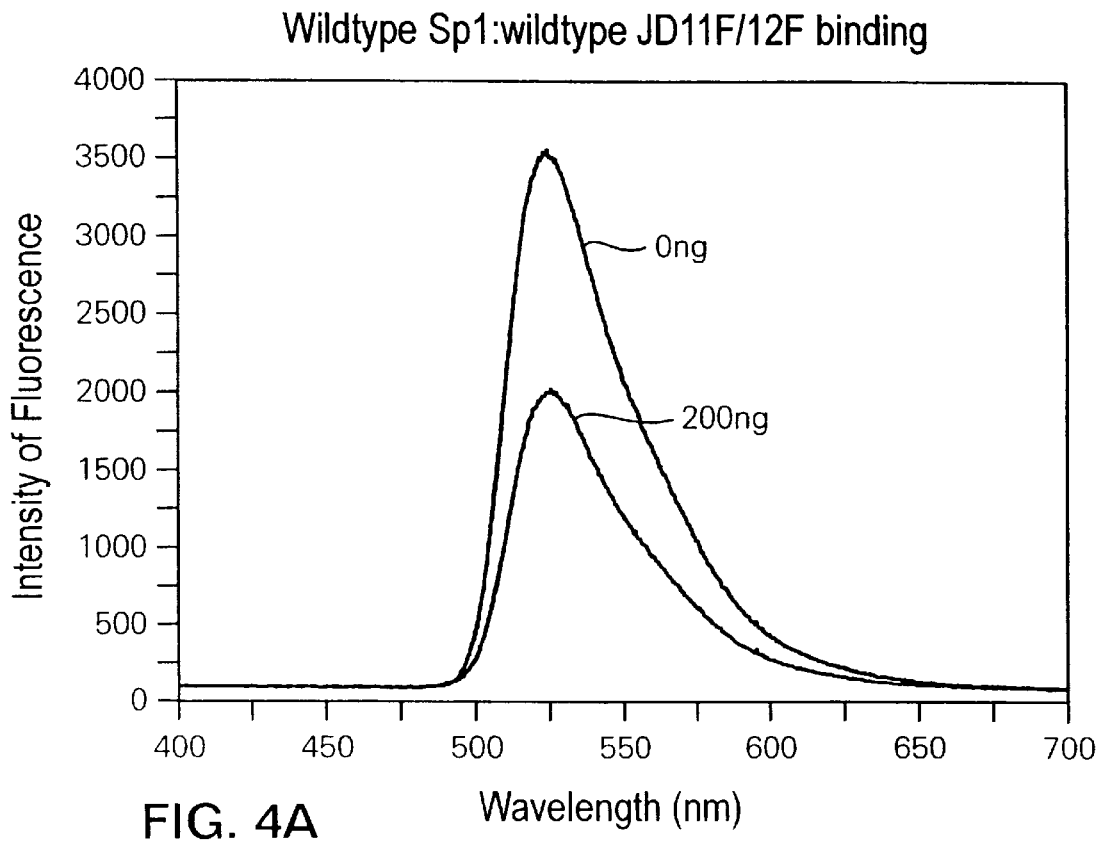

FIG. 4 illustrates the binding of the zinc finger DNA-binding protein Sp1 to wild-type JD11F/12F or mutant JD13F/14F. When 200 ng Sp1 was bound to 0.1 pmole JD11 F/12F, a 44% decrease in fluorescent intensity was observed, compared to the intensity level achieved with JD11F/12F alone (FIG. 4A). Furthermore, the binding of 25 ng of full length Sp1 protein could be reliably detected (data not shown), demonstrating the high sensitivity of the laser assay. Since Sp1 is a relatively large protein (95 KDa), while c-JUN is only 40 KDa in size, a lesser amount of protein was required to achieve a 44% reduction in fluorescent intensity for Sp1-bound DNA than c-JUN-bound DNA, due to greater absorption and retention of emitted fluorescent light by the larger protein.

When 200 ng Sp1 was reacted with 0.1 pmole mutant JD13F/14F, no decrease in fluorescent intensity was observed (FIG. 4B), indicating non-binding of protein to the mutated DNA sequence. These studies confirmed the specificity of the laser detection assay for a completely different class of DNA-binding proteins.

Example 5

This example illustrates the ability of the invention to study the binding of an antibody directed to a specific protein, which is directly bound to the labeled DNA sequence. Addition of specific antibodies to protein:DNA complexes (especially multi-protein:DNA complexes) is a technique used to identify the presence of unknown proteins in protein:DNA complexes. The binding of the antibody will either inhibit or totally prevent the protein:DNA complex from forming (resulting in a minimal decrease or no change in fluorescent intensity when compared to free DNA) or will result in an antibody:protein:DNA complex that decreases the intensity of fluorescence even more than the protein:DNA complex.

1 µg, 500 ng and 250 ng c-JUN were reacted with 0.075 pmole of wild-type JD1F/2F in the 50 mM NaCl or 50 mM KCl reaction mix as previously described. After a 15 minute incubation at 21° C., variable amounts of the monoclonal IgG$_1$, antibody, c-JUN (KM-1) (from Santa Cruz Biotechnology, Santa Cruz, Calif.), raised against a peptide corresponding to amino acids 56 to 69 of human c-JUN, was added to some of the c-JUN:DNA mixtures. The reaction mixtures were incubated for an additional 40 minutes at 21° C., placed into a quartz cuvette, irradiated with an argon ion laser beam having a wavelength of 488 nm and monitored for fluorescent emission.

Figure 5A:
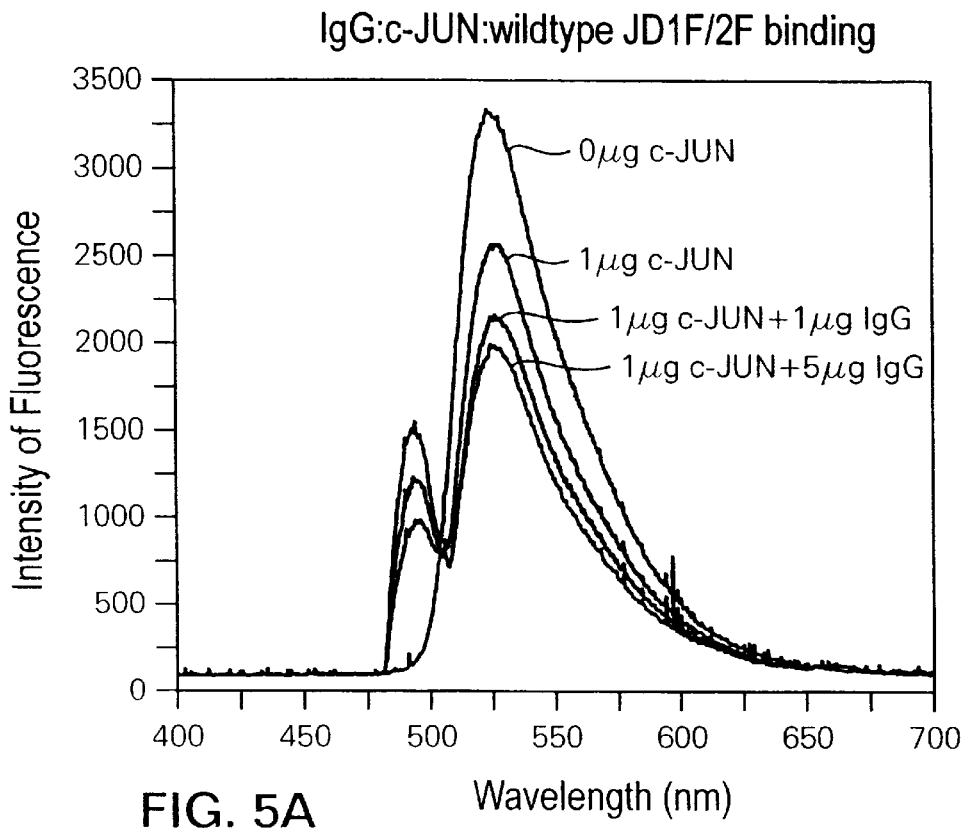
Figure 5B:
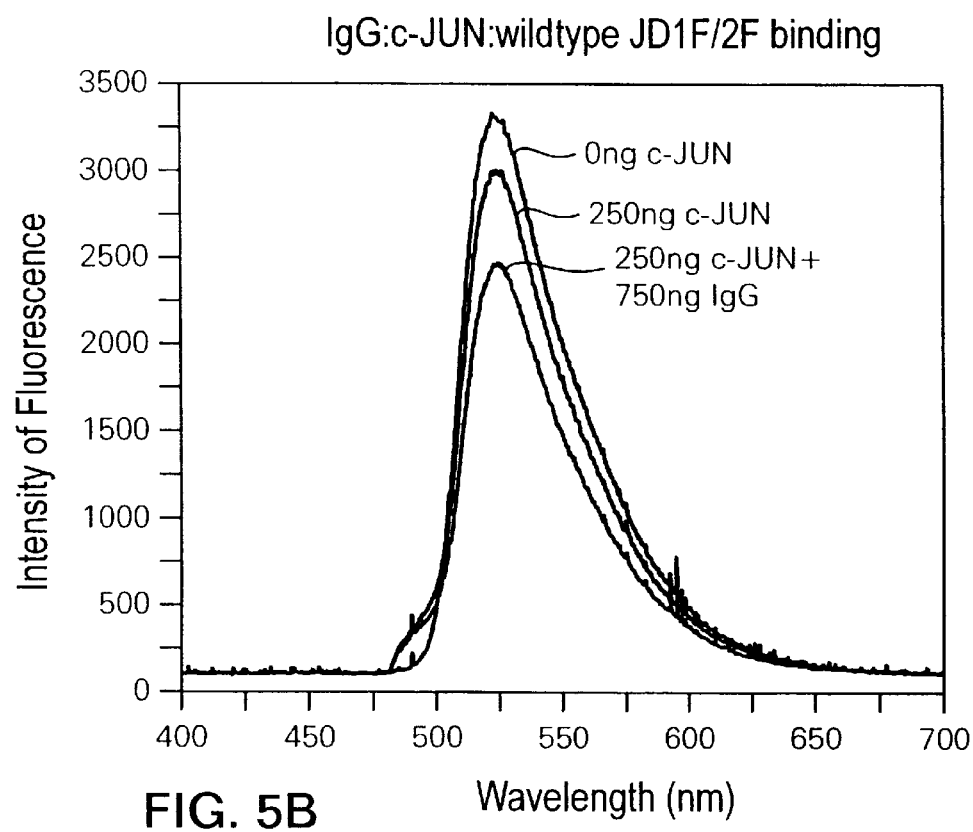

FIGS. 5A and 5B show the binding of 1 µg or 250 ng c-JUN to JD1F/2F, respectively, in the 50 mM NaCl reaction mix. When 1 µg or 250 ng c-JUN was bound to JD1F/2F, a 25% and 11% decrease in intensity, respectively, was observed, compared to the level achieved with DNA alone. Addition of 5 µg or 1 µg of c-JUN antibody to 1 µg c-JUN resulted in a 42% and 37% decrease, respectively (i.e., a further decrease of 17% and 12%), indicative of IgG:c-JUN:DNA complex formation (FIG. 5A). Identical decreases in intensity were observed when c-JUN antibody was bound to 1 µg c-JUN bound to JD1F/2F in the 50 mM KCl reaction mix (data not shown). Similarly, addition of 750 ng of c-JUN antibody to 250 ng c-JUN bound to JD1F/2F, yielded a 27% decrease in intensity, a further decrease of 16% from the level achieved from the protein:DNA complex alone (FIG. 5B). IgG:c-JUN complexes did not bind to mutant DNA JD3F/4F (data not shown), confirming the specificity of the laser assay.

This example demonstrates that the laser detection method can differentiate between an antibody:protein:DNA complex and a protein:DNA complex. Moreover, it establishes the ability of the invention to reliably detect heterologous multi-protein complexes bound to DNA and not just monomers or homodimers of protein bound to DNA. Only one of the proteins in the multi-protein:DNA complex needs to be bound to DNA. Multi-protein:DNA complexes, where more than one protein interacts with DNA can also be assayed by the invention.

Example 6

The ubiquitous cellular octamer-binding protein (Oct-1) binds DNA directly by its characteristic DNA-binding domain, which is completely different than the DNA-binding domains of c-JUN or Sp1. Oct-1 is a member of the POU domain DNA-binding proteins, which regulate cell-specific transcription and development. See, e.g., Sturm et al., "The ubiquitous octamer-binding protein Oct-1 contains a POU domain with a homeo box subdomain." 2 Genes and Development 1582–1599 (1988). The structure of the POU domain is unique among DNA-binding domains, because it contains two structurally independent domains that cooperate functionally as a single DNA-binding unit. Oct-1 binds to DNA via this POU domain, composed of a 75 amino acid POU-specific (POU$_S$) domain, a short linker region of 24 amino acids, and a 60 amino acid POU-type homeo (POU$_H$) domain. Both the POU$_S$ domain and the POU$_H$ domain contain helix-turn-helix (HTH) structures.

Unlike Examples 1–5,which used purified protein, this example uses HeLa cell nuclear extracts (from Promega, Madison, Wis.) as the source for Oct-1. The use of HeLa cell nuclear extracts, which contain a vast multitude of various DNA-binding proteins and transcription factors, shows the feasibility of using crude protein extracts to detect sequence-specific protein:DNA binding by the laser assay of the invention.

A wild-type fluorescein labeled dsDNA oligonucleotide, JD49F/50F, containing a single consensus 8 bp Oct-1 DNA binding site, was derived from the human immunoglobulin heavy chain promoter. Complementary 5'-fluorescein labeled ssDNA 18-mers JD49F and JD50F were synthesized, purified and annealed as above.

Sequence for wild-type JD49F (SEQ ID NO:11):
5'-Flu-GAG TAT GCA AAT CAT GTG-3'
Sequence for wild-type JD50F (SEQ ID NO:12):
5'-Flu-CAC ATG ATT TGC ATA CTC-3'

Mutant dsDNA 18-mer JD51F/52F was identical in sequence to wild-type JD49F/50F, except for a double point mutation ($A_1T_2 \rightarrow CG$) (underlined) that inactivated the POU$_S$ binding site, and a second double point mutation ($A_6A_7 \rightarrow CC$) (underlined) that inactivated the POU$_H$ binding site, thereby converting the consensus Oct-1 binding site ATGCAAAT to CGGCACCT.

Sequence for mutant JD51F (SEQ ID NO:13):
5'-Flu-GAG TCG GCA CCT CAT GTG-3'
Sequence for mutant JD52F (SEQ ID NO:14):
5'-Flu-CAC ATG AGG TGC CGA CTC-3'

The Oct-1:DNA binding reaction mixture (30 µl) contained the following: 9.25 mM HEPES, pH 7.9, 2.23 mM MgCl$_2$, 0.03 mM EDTA, 63 mM NaCl, 1.0 mM DTT, 3.75% (v/v) glycerol, 0.10 mg/ml BSA, 0.01 mM PMSF, 67 µg/ml poly(dI)-poly(dC), 67 µg/ml poly(dG-dC)-poly(dG-dC), 0–15 µg HeLa cell nuclear extract (Promega) and 0.05 pmole 5'-fluorescein labeled dsDNA oligonucleotide. The relatively high concentrations of poly(dI)-poly(dC) and poly(dG-dC)-poly(dG-dC) are required to ensure sequence specific protein:DNA binding, when using crude nuclear protein extracts. The reaction mixtures were incubated at 21° C. for 30 minutes, placed into a quartz cuvette, irradiated with an argon ion laser beam having a wavelength of 488 nm and monitored for fluorescent emission.

Figure 6A:
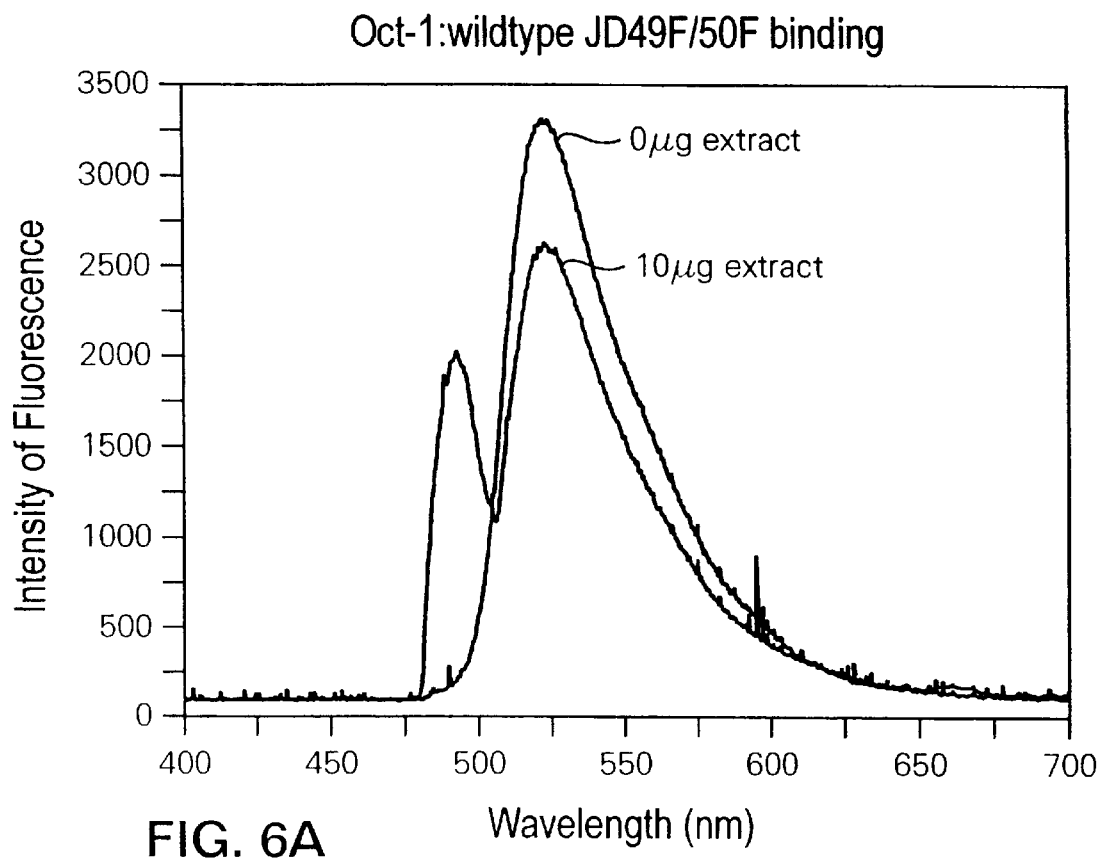
Figure 6B:
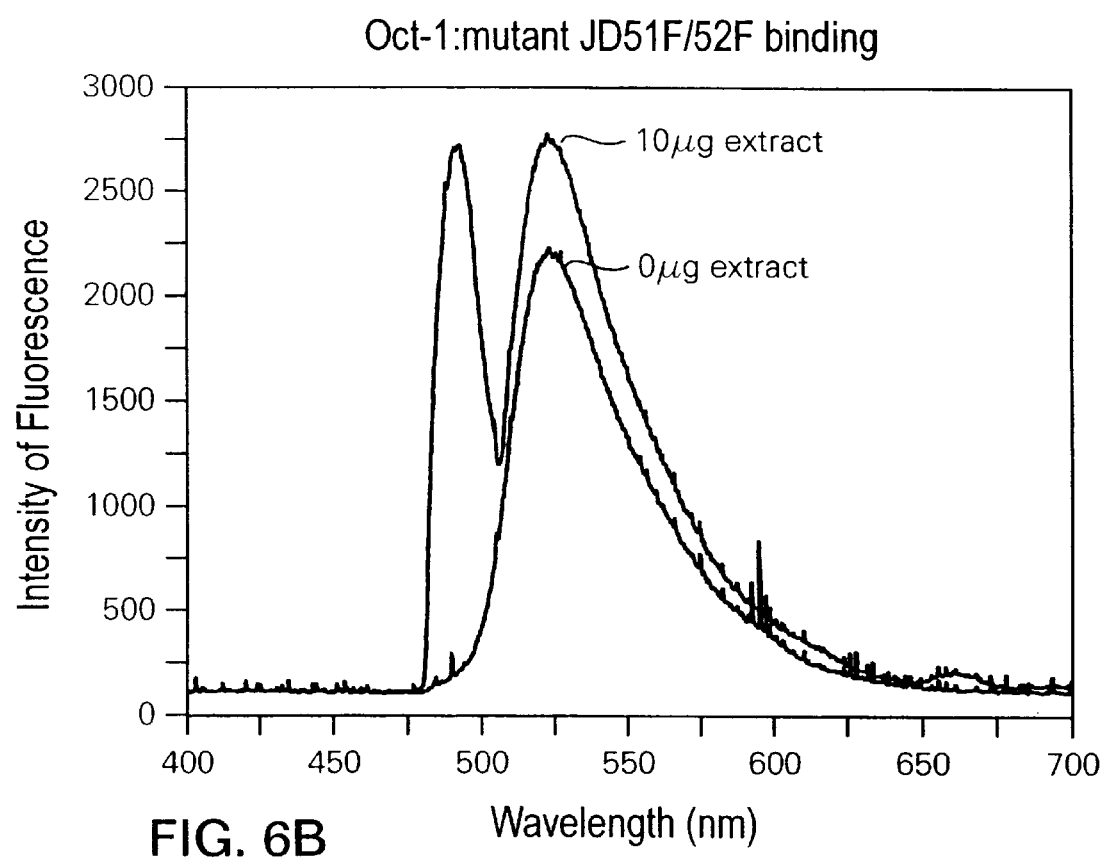

The fluorescent spectra obtained when 10 μg of HeLa cell nuclear extract was reacted with 0.05 pmole wild-type JD49F/50F or 0.05 pmole mutant JD51F/52F are shown in FIGS. 6A and 6B, respectively. The Oct-1 protein present in the HeLa cell nuclear extract, bound specifically to the wild-type high affinity Oct-1 binding site, resulting in a 22% decrease in fluorescent intensity compared to the level observed with JD49F/50F alone (FIG. 6A). By contrast, Oct-1 did not bind to mutant JD51F/52F, as indicated by the increase in fluorescent intensity above that observed with mutant DNA alone (FIG. 6B), confirming the sequence specificity of the laser binding assay. These experiments demonstrated the specificity of the laser detection assay for another completely different class of DNA-binding proteins.

Moreover, this example confirmed that specific protein:DNA binding may be reliably measured by the invention even when using crude HeLa cell nuclear extracts, that contain hundreds of other DNA-binding proteins. Specificity is conferred by the selection of the appropriately labeled DNA sequence, that recognizes the particular DNA-binding protein to be studied.

Example 7

This Example clearly demonstrates that the method of the invention can measure binding of a multi-protein complex (consisting of two or more different proteins) to one (or more) binding sites on a DNA sequence. Studies were conducted on the binding of the human cellular proteins octamer-binding protein (Oct-1) and host cellular factor (HCF—see, e.g., Wilson et al., "The VP16accessory protein HCF is a family of polypeptides processed from a large precursor protein." 74 Cell 115–125 (1993)) with the herpes simplex virus type 1 (HSV-1) protein VP16 (or Vmw65) to the DNA sequence TAATGARAT (where R is a purine). This multi-protein:DNA complex is called the immediate early complex (IEC) or VP 16-induced complex. Although VP 16 is the most potent trans-activator of genes ever identified, it cannot bind DNA efficiently on its own. Instead, it interacts specifically with Oct-1 and HCF to induce genes. VP 16 binds to Oct-1 and HCF via its amino terminal 411 amino acids. The C-terminal highly acidic domain of VP 16, defined by amino acids 411 to 490, functions as the potent transcriptional activating region. See, e.g., Dalrymple et al., "DNA sequence of the herpes simplex virus type 1 gene whose product is responsible for transcriptional activation of immediate early promoters." 13 Nucleic Acids Research 7865–7879 (1985).

Oct-1 binds to DNA via its bipartite POU domain, which is capable of displaying exceptional DNA sequence recognition flexibility. The Oct-1 POU domain binds to the octamer sequence ATGCAAAT as a monomer, with the $POU_S$ domain contacting the 5' half of this site (ATGC) and the $POU_H$ domain interacting with the 3' half of this site (AAAT) on opposite sides of the DNA. When Oct-1 is bound to the high affinity ATGCAAAT binding site, it is incapable of interacting with VP16.

Oct-1 also binds to DNA sites that bear little resemblance to the octamer consensus. For example, Oct-1 by itself or in association with HCF and VP16 can bind the DNA sequence TAATGARAT, which bears as little as a 4 of 8 bp match to the octamer consensus site. Two forms of the TAATGARAT site are found in the promoter sequences of the herpes simplex virus immediate early (HSV IE) genes. The first, designated the (OCTA$^+$)TAATGARAT motif, contains an overlapping octamer/TAATGARAT sequence, which binds Oct-1 with high affinity. The second, called (OCTA$^-$) TAATGARAT, lacks an overlapping octamer sequence and binds Oct-1 with relatively low affinity. The $POU_H$ domain of Oct-1 binds the 5' TAAT sequence, while the $POU_S$ domain binds the GARAT sequence on the (OCTA$^-$) TAATGARAT site. On the (OCTA$^+$)TAATGARAT binding site, the $POU_H$ domain remains fixed to the TAAT sequence, while the $POU_S$ domain can bind either the 5' ATGC sequence or the 3' GARAT element. The Oct-1 $POU_H$ domain is sufficient for interacting with VP16.

The HCF is required to stabilize the association of Oct-1with VP 16 on a TAATGARAT site, by first forming a stable complex with VP16 independent of Oct-1 or the TAATGARAT element. The exact mechanism by which HCF stabilizes VP16 association with Oct-1is unknown. The HCF may induce a conformational change within VP16, which primes VP16 to interact with Oct-1and the GARAT element of the TAATGARAT site. Alternatively, within the IEC complex, the HCF may contact Oct-1 or the DNA, and thus confer greater stability to the complex.

A wild-type fluorescein labeled dsDNA oligonucleotide, JD41F/42F, containing an (OCTA$^-$) TAATGARAT site was derived from a 20 bp region (−343 to −324) from the HSV-1 IE gene 4/5 promoter. Complementary 5'-fluorescein labeled ssDNA 20-mers JD41F and JD42F were synthesized, purified and annealed as above.

Sequence for wild-type JD41F (SEQ ID NO:15):

5'-Flu-GGC GGT AAT GAG ATA CGA GC-3'

Sequence for wild-type JD42F (SEQ ID NO:16):

5'-Flu-GCT CGT ATC TCA TTA CCG CC-3'

Mutant dsDNA 20-mer JD43F/44F was identical in sequence to wild-type JD41F/42F, except for a double point mutation ($A_2A_3$→CC) (underlined) that inactivated the $POU_H$ binding site, and a second double point mutation ($A_9T_9$→CG) (underlined) that inactivated the $POU_S$ binding site, thereby converting the Oct-1 binding site TAAT-GAGAT to TCCTGAGCG.

Sequence for mutant JD43F (SEQ ID NO:17):

5'-Flu-GGC GGT CCT GAG CGA CGA GC-3'

Sequence for mutant JD44F (SEQ ID NO:18):

5'-Flu-GCT CGT CGC TCA GGA CCG CC-3'

A wild-type fluorescein labeled dsDNA oligonucleotide, JD45F/46F, containing a (OCTA$^+$)TAATGARAT site was derived from a 23 bp region (−170 to −148) from the HSV-1 IE gene 1 Promoter. Complementary 5'-fluorescein labeled ssDNA 23-mers JD45F and JD46F were synthesized, purified and annealed as above.

Sequence for wild-type JD45F (SEQ ID NO:19):

5'-Flu-GTG CAT GCT AAT GAT ATT CTT TG-3'

Sequence for wild-type JD46F (SEQ ID NO:20):

5'-Flu-CAA AGA ATA TCA TTA GCA TGC AC-3'

Mutant dsDNA 23-mer JD47F/48F was identical in sequence to wild-type JD45F/46F, except for a double point mutation ($A_6A_7$→CC) (underlined) that inactivated the $POU_H$ binding site, and two additional double point mutations ($A_1T_2$→CG) and ($A_{12}T_{13}$→CG) (underlined) that inactivated the two $POU_S$ binding sites, thereby converting the Oct-1 binding site ATGCTAATGATAT to CGGCTCCT-GATCG.

Sequence for mutant JD47F (SEQ ID NO:21):

5'-Flu-GTG CCG GCT CCT GAT CGT CTT TG-3'

Sequence for mutant JD48F (SEQ ID NO:22):

5'-Flu-CAA AGA CGA TCA GGA GCC GGC AC-3'

The Oct-1:HCF:VP16:DNA binding reaction mixture (30 μl) contained the following: 9.25 mM HEPES, pH 7.9, 2.23 mM MgCl$_2$, 0.03 mM EDTA, 63 mM NaCl, 1.0 mM DTT, 3.75% (v/v) glycerol, 0.10 mg/ml BSA, 0.01 mM PMSF, 133 μg/ml-poly(dI)-poly(dC), 67 μg/ml poly(dG-dC)-poly (dG-dC), 0–25 μg HeLa cell nuclear extract (Promega), 0–0.1 μg HSV-1 virion extract and 0.025 pmole 5'-fluorescein labeled dsDNA oligonucleotide. The HSV-1 virion extract containing 80% pure VP16 was kindly provided by Dr. Chris Preston (MRC Institute of Virology, Glasgow, Scotland). HeLa cell nuclear extracts served as the source for Oct-1 and HCF. All components except the DNA and the virion extract were incubated at 21° C. for 10 minutes. DNA was then added, followed by the addition of HSV-1 virion extract (where appropriate). Reaction mixtures were incubated for an additional 30 minutes at 21° C., placed into a quartz cuvette, irradiated with an argon ion laser beam having a wavelength of 488 nm and monitored for fluorescent emission.

Figure 7A:
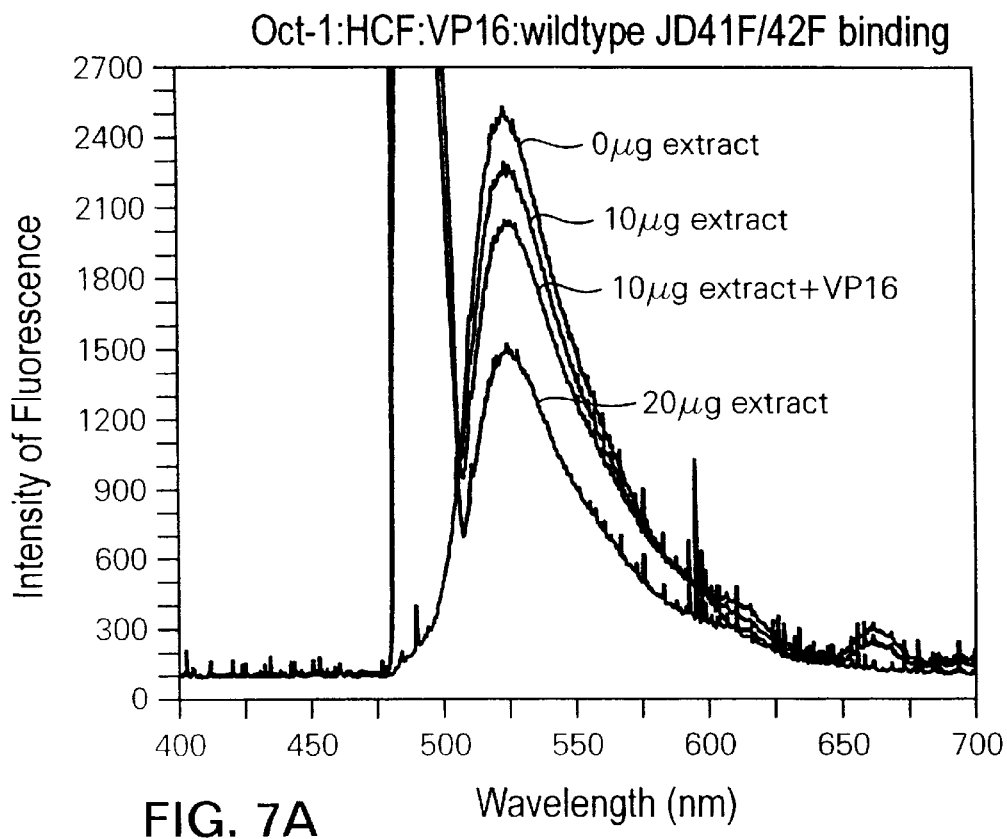

The Oct-1 protein, present in 10 μg and 20 μg of HeLa cell nuclear extract, bound specifically to 0.025 pmole wild-type JD41F/42F, resulting in a 10% and a 43% decrease, respectively, in fluorescent intensity compared to the level achieved with JD41F/42F alone (FIG. 7A). The low DNA amount of 0.025 pmole was in molar excess to the amount of Oct-1 present in the HeLa cell nuclear extract. The observation that 10 μg of HeLa cell nuclear extract produced a 22% decrease in fluorescent intensity when Oct-1 was bound to 0.05 pmole of its high affinity JD49F/50F binding site (in Example 6), whereas the same amount of HeLa cell nuclear extract resulted in only a 10% decrease in fluorescent intensity when Oct-1 was bound to 0.025 pmole of its low affinity JD41F/42F binding site (which is in molar excess to the amount of Oct-1 present), verified the ability of the laser binding assay to discriminate between high affinity and low affinity DNA binding sites for the same protein.

When 0.1 μg of VP16 was added to the Oct-1:JD41F/42F reaction mix, a 20% decrease in fluorescent intensity was observed, representing a further decrease of 10% from the level achieved from the Oct-1:JD41F/42F complex alone (FIG. 7A). This additional decrease arose from the multi-protein Oct-1:HCF:VP16:JD41F/42F complex formation, which was able to absorb and retain more emitted fluorescent light than the single protein Oct-1:JD41F/42F complex.

Figure 7B:
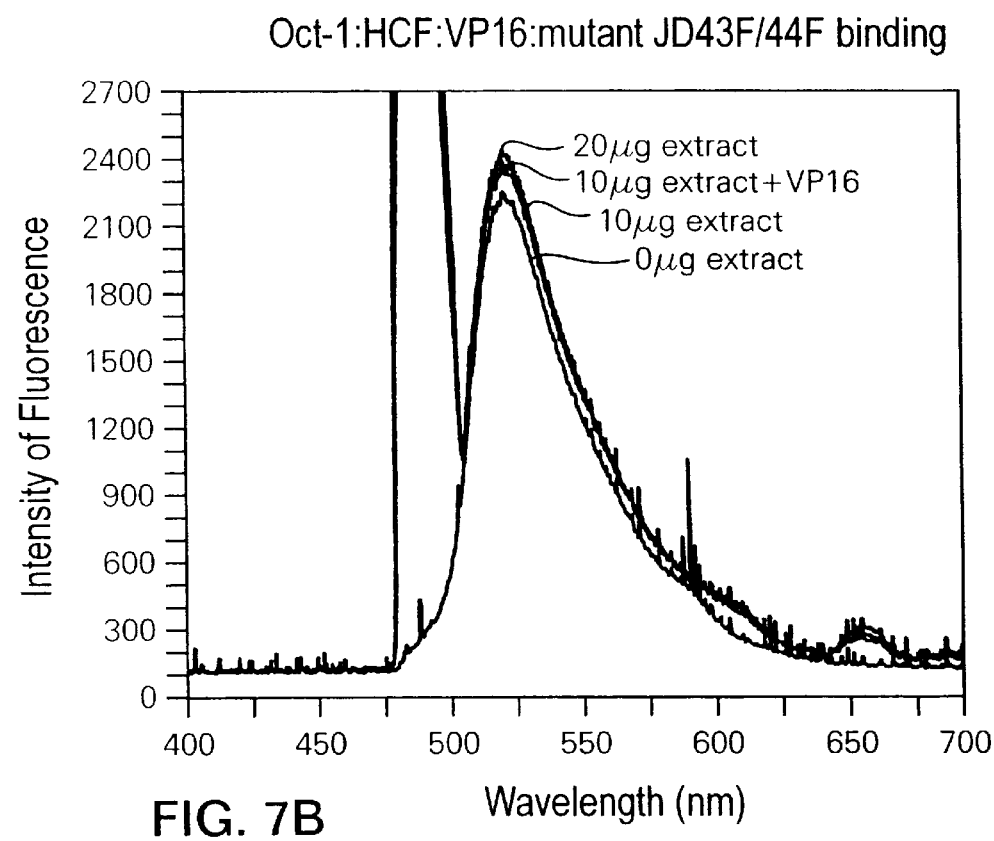

No decrease in fluorescent intensity was observed when 10 μg or 20 μg of HeLa cell nuclear extract, in the absence or presence of VP16, was reacted with 0.025 pmole mutant JD43F/44F, indicating non-binding of Oct-1 or Oct-1:HCF:VP16 complex to the mutated DNA sequence (FIG. 7B). These mutant DNA binding studies confirmed the specificity of the laser detection method for measuring specific multi-protein:DNA complex formation using crude nuclear extracts.

Figure 8A:
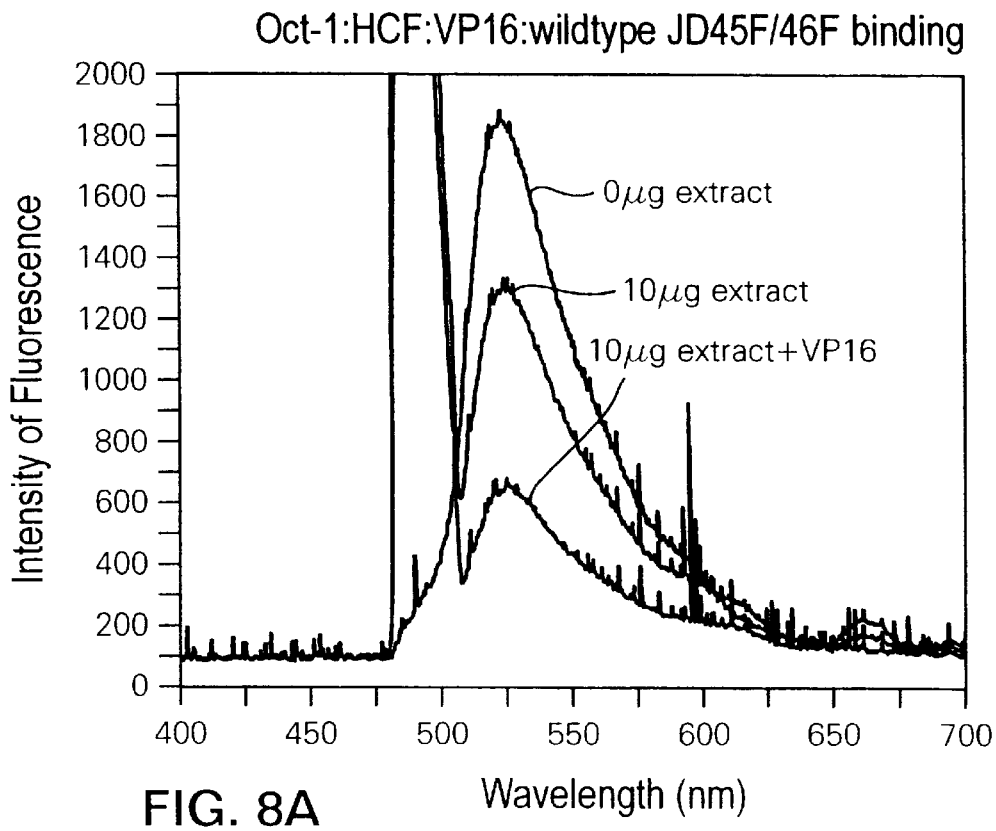

When 10 μg of HeLa cell nuclear extract was reacted with 0.025 pmole of wild-type JD45F/46F, a 32% decrease in fluorescent intensity occurred, compared to the fluorescent intensity observed with JD45F/46F alone (FIG. 8A). This relatively large decrease in intensity is a function of Oct-1's ability to bind with high affinity to the (OCTA$^+$) TAATGARAT site.

Addition of 0.1 μg of VP16 to 10 g HeLa cell nuclear extract and 0.025 pmole wild-type JD45F/46F, resulted in a 69% decrease in fluorescent intensity, representing a further decrease of 37% from the intensity level obtained from the Oct-1:JD45F/46F complex alone (FIG. 8A). Since Oct-1, HCF and VP16 are 110 KDa, ~300 KDa and 65 KDa in size, respectively, the huge 69% decrease is a direct result of highly efficient multi-protein Oct-1:HCF:VP16 binding to the (OCTA$^+$)TAATGARAT site present in JD45F/46F.

Figure 8B:
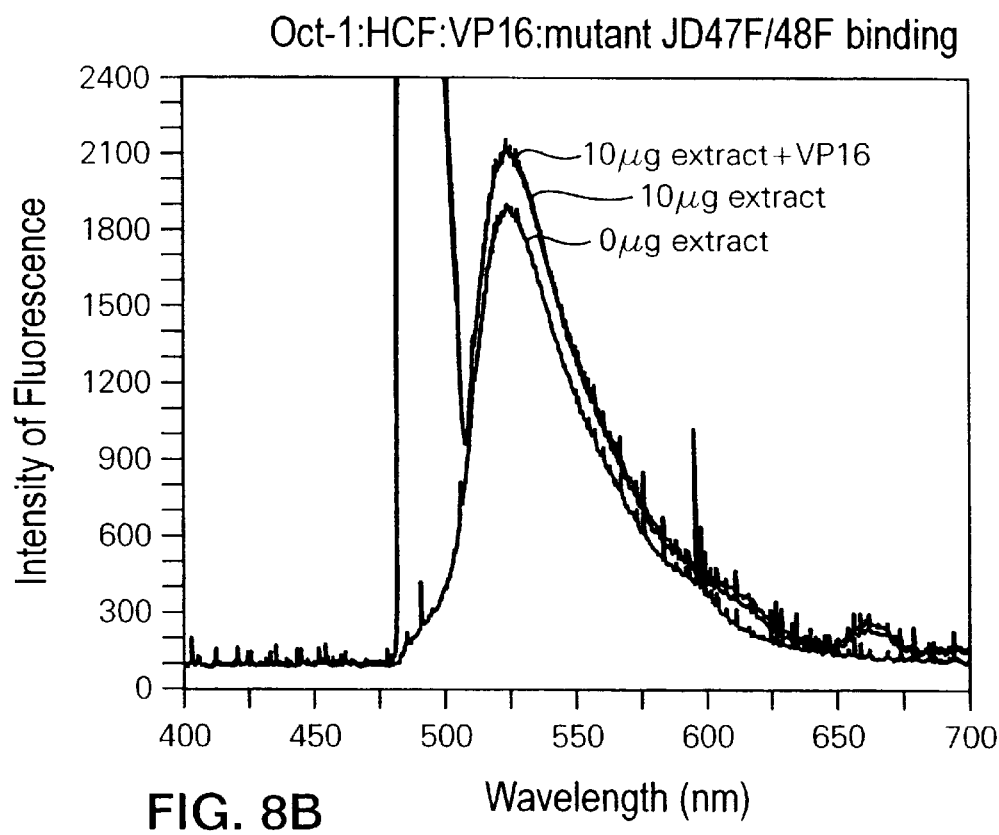

By contrast, no decrease in fluorescent intensity was observed when 10 μg of HeLa cell nuclear extract, in the absence or presence of 0.1 μg VP16, was reacted with 0.025 pmole mutant JD47F/48F (FIG. 8B), clearly indicating disruption of DNA binding to the mutated DNA sequence, and further proving the specificity of the laser binding assay.

This example clearly demonstrates that the method of the invention can reproducibly measure specific binding of a multi-protein complex (consisting of two or more different proteins) to one (or more) binding sites on a DNA sequence, when using crude nuclear cell extracts. Furthermore, the laser binding assay can evaluate the affinity of a specific protein or multi-protein complex to any given DNA sequence.

As demonstrated by the Examples, the invention is applicable to all classes of DNA-binding proteins. For example, when the oncoprotein c-JUN binds to its specific DNA recognition site, a 55% decrease in measurable units is observed, compared to the level achieved by unbound DNA (FIGS. 1A and 1B). No decrease is observed when c-JUN is reacted with a mutant DNA sequence (FIGS. 1C and 1D), indicating non-binding and confirming the specificity of the detection method.

Furthermore, specific binding of peptides containing just the DNA-binding domain of the protein can be detected in a quantitative manner. For example, 20 ng, 100 ng and 200 ng of c-JUN peptide bound to wild-type DNA results in 13%, 28% and 43% decreases, respectively, compared to the level observed for free DNA (FIG. 2A). The fact that the binding of just ng of c-JUN peptide can be reliably measured, demonstrates the high sensitivity of the detection assay. By contrast, 20 ng, 100 ng and 200 ng of c-JUN peptide do not bind mutant DNA, resulting in minor increases above the level observed with mutant DNA alone (FIG. 2B). Binding of peptides in lieu of full length proteins may be of particular interest to designing and/or screening pharmaceuticals.

The specificity of the detection assay was further tested by reacting a mutant c-JUN DNA-binding domain peptide with wild-type (FIG. 3A) or mutant DNA (FIG. 3B). No decrease was observed, even when a vast excess of c-JUN mutant 14 peptide was present, clearly demonstrating disruption of DNA binding and further proving the specificity of the assay.

Figure 4B:
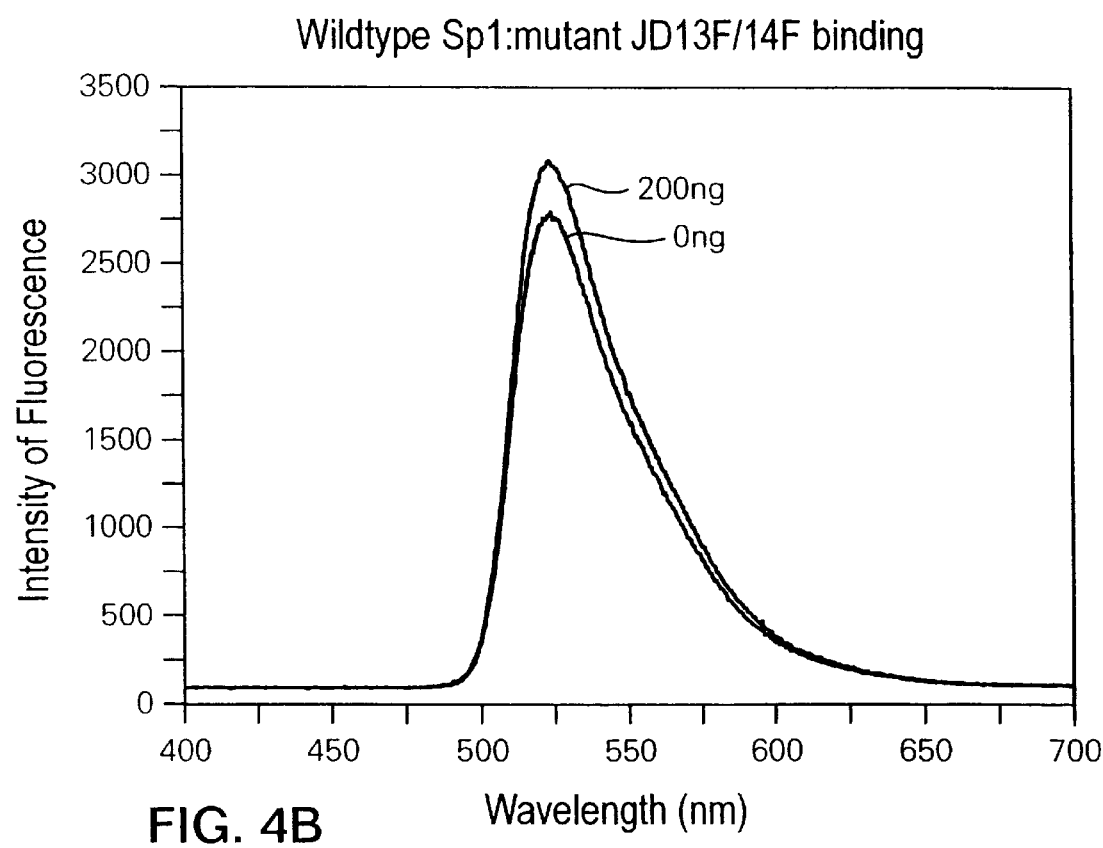

FIGS. 4A and 4B illustrate the binding of the zinc finger DNA-binding protein Sp1 to wild-type or mutant DNA binding sites, respectively. When 200 ng of Sp1 is bound to wild-type DNA, a 44% decrease is observed, compared to the level measured for DNA alone. Non-binding of 200 ng Sp1 is observed for the mutated DNA sequence.

The laser detection assay can differentiate between an antibody:protein:DNA complex and a protein:DNA complex. For example, a 42% and 37% decrease in fluorescent intensity was observed when 5 μg or 1 μg of c-JUN antibody, respectively, was bound to 1 μg c-JUN complexed to wild-type DNA, compared to the 25% decrease obtained for c-JUN:DNA complexes (FIG. 5A). IgG:c-JUN complexes did not bind to mutant DNA sequences.

FIGS. 6, 7 and 8 illustrate the binding of the bipartite POU domain DNA-binding protein Oct-1 to three different DNA sequence recognition sites, with different binding affinities. Moreover, Examples 6–7 Prove the feasibility of using crude nuclear protein extracts as a source of DNA-binding proteins, while still retaining highly specific protein-DNA binding. Depending on the binding affinity of each DNA site, 10 μg of HeLa cell nuclear extracts bound wild-type Oct-1 DNA binding sites with a 10%, 22% or 32% decrease, compared to levels achieved for unbound DNA.

Significantly, the method of the invention can reliably measure the binding of multi-protein complexes (consisting of two or more different proteins) to one (or more) DNA binding sites, whether pure proteins or crude nuclear extracts are used. For example, Oct-1:HCF:VP16:DNA complexes yielded a 69% and 20% decrease in fluorescent intensity when bound to a high affinity (OCTA$^+$)TAATGARAT site or a low affinity (OCTA$^-$)TAATGARAT site, respectively (FIGS. 8 and 7). Non-binding of Oct-1 protein or Oct-1:HCF:VP16 Protein complex is observed for all of the mutated DNA sequences.

Multi-protein:DNA complexes are much more prevalent in nature and biologically significant than single protein:DNA complexes. The ability of the method of the invention to employ crude nuclear protein extracts to assay single or multi-protein binding to DNA in a highly specific manner is of major clinical relevance.

While the invention has been described in detail and with reference to specific examples thereof, it will be apparent to one skilled in the art that various changes and modifications can be made therein without departing from the spirit and scope thereof.

What is claimed is:

1. A method for assaying binding between at least one fluorophore-labeled compound and at least one unlabeled compound, said method comprising detecting a quenching effect on fluorescence emitted by said at least one fluorophore-labeled compound resulting from said binding, said quenching effect detecting comprising:

provinding a test medium comprising said at least one fluorophore-labeled compound and said at least one unlabeled compound;

irradiating said test medium with radiation effective to cause said at least one fluorophore-labeled compound to emit fluorescent light; and comparing a fluorescent intensity of said fluorescent light with a reference fluorescent intensity of a reference medium, wherein said quenching effect and said specific binding are detected when said fluorescent intensity is less than said reference fluorescent intensity, wherein:

(a) said binding is specific and other than nucleobase to nucleobase;

(b) said method is conducted:
  (i) without separating complexes of said at least one fluorophore-labeled compound and said at least one unlabeled compound from said at least one fluorophore-labeled compound prior to said quenching effect detecting; and
  (ii) without providing a signal quenching agent to quench said emitted fluorescence; and (c) said at least one fluorophore-labeled compound is:
  (i) a labeled nucleic acid to which said fluorophore is covalently bound and said at least one unlabeled compound is an unlabeled protein; or
  (ii) a labeled protein and said at least one unlabeled compound is an unlabeled nucleic acid.

2. The method of claim 1, wherein said labeled nucleic acid and said unlabeled nucleic acid are selected from the group consisting of dsDNA, ssDNA, kNA, ssRNA, dsRNA, mRNA, hnRNA, tRNA, rRNA, ssDNA:RNA hybrids, dsDNA:RNA hybrids, nucleic acid analogues and oligonucleotides.

3. The method of claim 1, wherein said labeled protein and said unlabeled protein are provided in a form of a purified preparation, a synthesized preparation, a semi-purified protein extract, a crude protein extract, or an in vitro translated preparation.

4. The method of claim 1, wherein said at least one unlabeled compound is a peptide, polypeptide, protein or multi-protein complex.

5. The method of claim 1, wherein said at least one fluorophore-labeled compound is said labeled protein and said at least one unlabeled compound is said unlabeled nucleic acid.

6. The method of claim 1, wherein said at least one fluorophore-labeled compound is said labeled nucleic acid and said at least one unlabeled compound is said unlabeled protein.

7. The method of claim 1, further comprising determining a binding affinity of said at least one labeled compound for a plurality of different unlabeled compounds.

8. The method of claim 7, wherein said at least one labeled compound is said labeled nucleic acid and said plurality of different unlabeled compounds are proteins.

9. The method of claim 8, further comprising selecting a drug candidate from among said plurality of different unlabeled proteins based on said binding affinity determination.

10. The method of claim 8, further comprising selecting a gene suppressing or activating agent from among said plurality of different unlabeled proteins based on said binding affinity determination.

11. The method of claim 8, further comprising comparing the binding affinities of said plurality of different unlabeled proteins to determine whether said proteins bind equivalently.

12. The method of claim 1, wherein said at least one fluorophore-labeled compound is said labeled nucleic acid and said at least one unlabeled compound is at least two proteins which form a multi-protein complex with said labeled nucleic acid.

13. The method of claim 12, wherein said multi-protein complex comprises said at least two proteins respectively bound to at least two adjacent sites on said labeled nucleic acid, and said method further comprises determining whether said at least two proteins bind to said at least two adjacent sites independently, cooperatively or synergistically.

14. The method of claim 12, wherein said multi-protein complex comprises said at least two proteins respectively bound to at least two sites on said labeled nucleic acid, said two sites being separated by intervening nucleic acid sequences that loop-out when the two bound proteins interact with one another.

15. The method of claim 6, wherein said method further comprises detecting binding of a protein-binding compound to said unlabeled protein.

16. The method of claim 15, wherein said protein-binding compound is an antibody specifically directed against said unlabeled protein.

17. The method of claim 16, wherein said protein-antibody binding is detected when fluorescent intensity is quenched by said binding of said antibody to said unlabeled protein and said unlabeled protein to said labeled nucleic acid.

18. The method of claim 16, wherein said protein-antibody binding is detected when fluorescent intensity is not quenched, said lack of quenching indicating that a protein-antibody complex has formed and hindered binding of said labeled nucleic acid to said unlabeled protein.

19. The method of claim 1, further comprising conducting a competitive assay between said labeled nucleic acid and at least one fluorophore-free nucleic acid by adding said fluorophore-free nucleic acid to said test medium.

20. The method of claim 1, wherein said at least one unlabeled compound is a mutant.

21. The method of claim 1, wherein said at least one labeled compound is a mutant.

22. The method of claim 1, wherein said at least one unlabeled compound is a mutant protein within a multi-protein complex, said at least one unlabeled compound hindering binding of another protein to said at least one fluorophore-labeled compound.

23. The method of claim 4, wherein said at least one unlabeled compound is modified by phosphorylation, glycosylation or interaction with metal ions.

24. The method of claim 7, further comprising identifying within a protein extract a presence of a functional protein or multi-protein complex which can bind DNA during different metabolic states of protein extract preparation.

25. The method of claim 8, wherein said labeled nucleic acid is modified.

26. The method of claim 25, wherein said labeled nucleic acid is methylated.

27. The method of claim 1, wherein said reference medium differs from said test medium in that said reference medium is devoid of said at least one unlabeled compound.

* * * * *

SEQUENCE LISTING

<160> NUMBER OF SEQ ID NOS: 22

<210> SEQ ID NO 1
<211> LENGTH: 17
<212> TYPE: DNA
<213> ORGANISM: Human

<400> SEQUENCE: 1
gtgtctgact catgctt                                                17

<210> SEQ ID NO 2
<211> LENGTH: 17
<212> TYPE: DNA
<213> ORGANISM: Human

<400> SEQUENCE: 2
aagcatgagt cagacac                                                17

<210> SEQ ID NO 3
<211> LENGTH: 17
<212> TYPE: DNA
<213> ORGANISM: Human

<400> SEQUENCE: 3
gtgtcttact catgctt                                                17

<210> SEQ ID NO 4
<211> LENGTH: 17
<212> TYPE: DNA
<213> ORGANISM: Human

<400> SEQUENCE: 4
aagcatgagt aagacac                                                17

<210> SEQ ID NO 5
<211> LENGTH: 132
<212> TYPE: PRT
<213> ORGANISM: Human

<400> SEQUENCE: 5

Gln Pro Gln Gln Gln Gln Gln Pro Pro His His Leu Pro Gln Gln Met
 1               5                  10                  15

Pro Val Gln His Pro Arg Leu Gln Ala Leu Lys Glu Glu Pro Gln Thr
                20                  25                  30

Val Pro Glu Met Pro Gly Glu Thr Pro Pro Leu Ser Pro Ile Asp Met
            35                  40                  45

Glu Ser Gln Glu Arg Ile Lys Ala Glu Arg Lys Arg Met Arg Asn Arg
        50                  55                  60

```
Ile Ala Ala Ser Lys Cys Arg Lys Arg Lys Leu Glu Arg Ile Ala Arg
 65                  70                  75                  80

Leu Glu Glu Lys Val Lys Thr Leu Lys Ala Gln Asn Ser Glu Leu Ala
                 85                  90                  95

Ser Thr Ala Asn Met Leu Arg Glu Gln Val Ala Gln Leu Lys Gln Lys
            100                 105                 110

Val Met Asn His Val Asn Ser Gly Cys Gln Leu Met Leu Thr Gln Gln
        115                 120                 125

Leu Gln Thr Phe
    130

<210> SEQ ID NO 6
<211> LENGTH: 132
<212> TYPE: PRT
<213> ORGANISM: Human

<400> SEQUENCE: 6

Gln Pro Gln Gln Gln Gln Pro Pro His His Leu Pro Gln Gln Met
  1               5                  10                  15

Pro Val Gln His Pro Arg Leu Gln Ala Leu Lys Glu Pro Gln Thr
                 20                  25                  30

Val Pro Glu Met Pro Gly Glu Thr Pro Pro Leu Ser Pro Ile Asp Met
            35                  40                  45

Glu Ser Gln Glu Arg Ile Lys Ala Glu Arg Lys Arg Met Arg Asn Arg
 50                  55                  60

Ile Ala Ala Ser Ile Asp Arg Lys Arg Lys Leu Glu Arg Ile Ala Arg
 65                  70                  75                  80

Leu Glu Glu Lys Val Lys Thr Leu Lys Ala Gln Asn Ser Glu Leu Ala
                 85                  90                  95

Ser Thr Ala Asn Met Leu Arg Glu Gln Val Ala Gln Leu Lys Gln Lys
            100                 105                 110

Val Met Asn His Val Asn Ser Gly Cys Gln Leu Met Leu Thr Gln Gln
        115                 120                 125

Leu Gln Thr Phe
    130

<210> SEQ ID NO 7
<211> LENGTH: 20
<212> TYPE: DNA
<213> ORGANISM: Human

<400> SEQUENCE: 7
ccggccgggg cggggctttt                                          20

<210> SEQ ID NO 8
<211> LENGTH: 20
<212> TYPE: DNA
<213> ORGANISM: Human

<400> SEQUENCE: 8
aaaagccccg ccccggccgg                                          20

<210> SEQ ID NO 9
<211> LENGTH: 20
<212> TYPE: DNA
<213> ORGANISM: Human

<400> SEQUENCE: 9
```

-continued ccggcctaaa tagggctttt                                          20

<210> SEQ ID NO 10
<211> LENGTH: 20
<212> TYPE: DNA
<213> ORGANISM: Human

<400> SEQUENCE: 10
aaaagcccta tttaggccgg                                          20

<210> SEQ ID NO 11
<211> LENGTH: 18
<212> TYPE: DNA
<213> ORGANISM: Human

<400> SEQUENCE: 11
gagtatgcaa atcatgtg                                            18

<210> SEQ ID NO 12
<211> LENGTH: 18
<212> TYPE: DNA
<213> ORGANISM: Human

<400> SEQUENCE: 12
cacatgattt gcatactc                                            18

<210> SEQ ID NO 13
<211> LENGTH: 18
<212> TYPE: DNA
<213> ORGANISM: Human

<400> SEQUENCE: 13
gagtcggcac ctcatgtg                                            18

<210> SEQ ID NO 14
<211> LENGTH: 18
<212> TYPE: DNA
<213> ORGANISM: Human

<400> SEQUENCE: 14
cacatgaggt gccgactc                                            18

<210> SEQ ID NO 15
<211> LENGTH: 20
<212> TYPE: DNA
<213> ORGANISM: Herpes Simplex Virus Type I

<400> SEQUENCE: 15
ggcggtaatg agatacgagc                                          20

<210> SEQ ID NO 16
<211> LENGTH: 20
<212> TYPE: DNA
<213> ORGANISM: Herpes Simplex Virus Type I

<400> SEQUENCE: 16
gctcgtatct cattaccgcc                                          20

<210> SEQ ID NO 17
<211> LENGTH: 20
<212> TYPE: DNA
<213> ORGANISM: Herpes Simplex Virus Type I

<400> SEQUENCE: 17

```
ggcggtcctg agcgacgagc                                          20

<210> SEQ ID NO 18
<211> LENGTH: 20
<212> TYPE: DNA
<213> ORGANISM: Herpes Simplex Virus Type I

<400> SEQUENCE: 18
gctcgtcgct caggaccgcc                                          20

<210> SEQ ID NO 19
<211> LENGTH: 23
<212> TYPE: DNA
<213> ORGANISM: Herpes Simplex Virus Type I

<400> SEQUENCE: 19
gtgcatgcta atgatattct ttg                                      23

<210> SEQ ID NO 20
<211> LENGTH: 23
<212> TYPE: DNA
<213> ORGANISM: Herpes Simplex Virus Type I

<400> SEQUENCE: 20
caaagaatat cattagcatg cac                                      23

<210> SEQ ID NO 21
<211> LENGTH: 23
<212> TYPE: DNA
<213> ORGANISM: Herpes Simplex Virus Type I

<400> SEQUENCE: 21
gtgccggctc ctgatcgtct ttg                                      23

<210> SEQ ID NO 22
<211> LENGTH: 23
<212> TYPE: DNA
<213> ORGANISM: Herpes Simplex Virus Type I

<400> SEQUENCE: 22
caaagacgat caggagccgg cac                                      23
```